United States Patent
Abbott et al.

(10) Patent No.: US 12,146,106 B2
(45) Date of Patent: Nov. 19, 2024

(54) PYROLYSIS OF PLASTIC WASTE TO PRODUCE LIGHT GASEOUS HYDROCARBONS AND INTEGRATION WITH AN ETHYLENE CRACKER

(71) Applicant: CHEVRON PHILLIPS CHEMICAL COMPANY LP, The Woodlands, TX (US)

(72) Inventors: Ronald G. Abbott, Porter, TX (US); Bruce D. Murray, Kingwood, TX (US); Scott G. Morrison, Kingwood, TX (US); Bradley T. Price, Kingwood, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 81 days.

(21) Appl. No.: 17/658,921

(22) Filed: Apr. 12, 2022

(65) Prior Publication Data
US 2022/0340820 A1 Oct. 27, 2022

Related U.S. Application Data

(60) Provisional application No. 63/175,978, filed on Apr. 16, 2021.

(51) Int. Cl.
*C10G 1/00* (2006.01)
*C07C 4/04* (2006.01)
(Continued)

(52) U.S. Cl.
CPC ............... *C10G 1/002* (2013.01); *C07C 4/04* (2013.01); *C08F 10/02* (2013.01); *C10B 53/07* (2013.01);
(Continued)

(58) Field of Classification Search
CPC .......... C10G 1/002; C10G 1/086; C10G 1/10; C10G 11/18; C10G 2300/1003;
(Continued)

(56) References Cited

U.S. PATENT DOCUMENTS

| | | | |
|---|---|---|---|
| 3,901,951 A | 8/1975 | Nishizaki | |
| 4,851,601 A | 7/1989 | Fukuda | |

(Continued)

FOREIGN PATENT DOCUMENTS

| | | |
|---|---|---|
| CA | 2202941 | 10/1978 |
| EP | 0607862 A1 | 7/1994 |

(Continued)

OTHER PUBLICATIONS

Second Written Opinion issued in corresponding PCT Application No. PCT/US2022/024433, mailed on Jun. 7, 2023, 7 pp.
(Continued)

*Primary Examiner* — Latosha Hines
(74) *Attorney, Agent, or Firm* — Eversheds Sutherland (US) LLP

(57) ABSTRACT

Processes for using pyrolysis gas as a feedstock or a co-feedstock for making a variety of chemicals, for example, circular ethylene, circular ethylene polymers and copolymers, and other circular products. In these processes, pyrolysis reactor conditions can be selected to increase or optimized the production of pyrolysis gas over pyrolysis oil, and the pyrolysis gas which is usually used as fuel or flared can be fed downstream of the steam cracker furnace for economic use to form circular chemicals. Operating parameters of the pyrolysis unit may be adjusted to increase or decrease the proportion of pyrolysis gas relative to pyrolysis liquid as a function of their relative economic values.

36 Claims, 1 Drawing Sheet

(51) Int. Cl.

| | |
|---|---|
| *C08F 10/02* | (2006.01) |
| *C10B 53/07* | (2006.01) |
| *C10B 57/06* | (2006.01) |
| *C10G 1/10* | (2006.01) |
| *C10G 9/36* | (2006.01) |
| *C10G 11/18* | (2006.01) |
| *C10L 1/06* | (2006.01) |
| *C10L 1/08* | (2006.01) |
| *C10L 3/06* | (2006.01) |

(52) U.S. Cl.
CPC ............. *C10B 57/06* (2013.01); *C10G 1/10* (2013.01); *C10G 9/36* (2013.01); *C10G 11/18* (2013.01); *C10L 1/06* (2013.01); *C10L 1/08* (2013.01); *C10L 3/06* (2013.01); C10G 2300/1003 (2013.01); C10G 2300/4081 (2013.01); C10G 2400/02 (2013.01); C10G 2400/04 (2013.01); C10G 2400/20 (2013.01); C10G 2400/26 (2013.01); C10G 2400/30 (2013.01); C10L 2200/0461 (2013.01); C10L 2270/023 (2013.01); C10L 2270/026 (2013.01)

(58) Field of Classification Search
CPC ........ C10G 2300/4081; C10G 2400/02; C10G 2400/04; C10G 2400/20; C10G 2400/26; C10G 2400/30; C10G 50/00; C10G 51/04; C10G 57/02; C10G 63/04; C10G 9/36; C07C 4/04; C08F 10/02; C10B 53/07; C10B 57/06; C10L 1/06; C10L 1/08; C10L 2200/0461; C10L 2270/023; C10L 2270/026; C10L 3/06
See application file for complete search history.

(56) References Cited

U.S. PATENT DOCUMENTS

| | | | |
|---|---|---|---|
| 5,216,149 | A | 6/1993 | Evans |
| 5,253,479 | A | 10/1993 | Di Cintio |
| 5,300,704 | A | 4/1994 | Evans |
| 5,321,174 | A | 6/1994 | Evans |
| 5,359,061 | A | 10/1994 | Evans |
| 5,359,099 | A | 10/1994 | Evans |
| 5,364,995 | A | 11/1994 | Kirkwood |
| 5,481,052 | A | 1/1996 | Hardman |
| 5,608,136 | A | 3/1997 | Maezawa |
| 5,639,937 | A | 6/1997 | Hover |
| 5,705,724 | A | 1/1998 | Collins |
| 5,731,483 | A | 3/1998 | Stabel |
| 5,821,553 | A | 10/1998 | Evans |
| 5,849,964 | A | 12/1998 | Holighaus |
| 5,904,838 | A | 5/1999 | Kalnes |
| 6,150,577 | A | 11/2000 | Miller |
| 6,822,126 | B2 | 11/2004 | Miller |
| RE40,124 | E | 3/2008 | Kaiser |
| 7,834,226 | B2 | 11/2010 | Miller |
| 8,088,961 | B2 | 1/2012 | Miller |
| 8,404,912 | B1 | 3/2013 | Miller |
| 8,480,880 | B2 | 7/2013 | Miller |
| 8,552,245 | B2 | 10/2013 | Simon |
| 8,696,994 | B2 | 4/2014 | Miller |
| 9,428,695 | B2 | 8/2016 | Narayanaswamy |
| 9,447,332 | B2 | 9/2016 | Narayanaswamy |
| 9,650,131 | B2 | 5/2017 | Jaber |
| 10,301,235 | B1 | 5/2019 | Cavinaw |
| 10,442,997 | B2 | 10/2019 | Narayanaswamy |
| 10,513,661 | B2 | 12/2019 | Narayanaswamy |
| 2009/0151233 | A1 | 6/2009 | Miller |
| 2009/0170739 | A1 | 7/2009 | Miller |
| 2011/0020190 | A1 | 1/2011 | Miller |
| 2011/0289826 | A1 | 12/2011 | Srinakruang |
| 2012/0184787 | A1 | 7/2012 | Miller |
| 2014/0228204 | A1 | 8/2014 | Narayanaswamy |
| 2014/0228205 | A1 | 8/2014 | Narayanaswamy |
| 2014/0228605 | A1 | 8/2014 | Narayanaswamy |
| 2014/0228606 | A1 | 8/2014 | Narayanaswamy |
| 2016/0090539 | A1 | 3/2016 | Frey |
| 2016/0264874 | A1 | 9/2016 | Narayanaswamy |
| 2016/0264883 | A1 | 9/2016 | Narayanaswamy |
| 2016/0264885 | A1 | 9/2016 | Narayanaswamy |
| 2016/0362609 | A1 | 12/2016 | Ward |
| 2017/0044465 | A1 | 2/2017 | Scheibel |
| 2017/0247617 | A1 | 8/2017 | Schenk |
| 2018/0002609 | A1 | 1/2018 | Narayanaswamy |
| 2018/0187087 | A1 | 7/2018 | Atkins |
| 2019/0023999 | A1 | 1/2019 | Sundaram |
| 2019/0161683 | A1 | 5/2019 | Narayanaswamy |
| 2019/0177626 | A1 | 6/2019 | Ramamurthy |
| 2019/0177652 | A1 | 6/2019 | Atkins |
| 2019/0233744 | A1 | 8/2019 | Narayanaswamy |
| 2019/0241838 | A1 | 8/2019 | Scheibel |
| 2019/0299491 | A1 | 10/2019 | Stanislaus |
| 2019/0367428 | A1 | 12/2019 | Ramamurthy |
| 2020/0017772 | A1 | 1/2020 | Ramamurthy |
| 2020/0017773 | A1 | 1/2020 | Ramamurthy |
| 2020/0080009 | A1 | 3/2020 | Derks |
| 2020/0181498 | A1 | 6/2020 | Heeres |
| 2020/0308492 | A1 | 10/2020 | Streiff |
| 2020/0362248 | A1 | 11/2020 | Cartolano |
| 2020/0369965 | A1* | 11/2020 | Bitting ............... C10G 9/24 |
| 2020/0369966 | A1 | 11/2020 | Bitting |
| 2021/0032545 | A1 | 2/2021 | Harandi |
| 2021/0061972 | A1 | 3/2021 | Nagy |
| 2021/0070958 | A1 | 3/2021 | Brita |
| 2021/0070959 | A1 | 3/2021 | Brita |
| 2021/0108154 | A1 | 4/2021 | John |
| 2021/0130262 | A1 | 5/2021 | Wu |
| 2021/0130698 | A1 | 5/2021 | Sundaram |
| 2021/0130699 | A1 | 5/2021 | Bitting |
| 2021/0130700 | A1 | 5/2021 | Wu |
| 2021/0139620 | A1 | 5/2021 | Slivensky |
| 2021/0189248 | A1 | 6/2021 | Timken |
| 2021/0189249 | A1 | 6/2021 | Timken |
| 2021/0189250 | A1 | 6/2021 | Timken |
| 2021/0189251 | A1 | 6/2021 | Timken |
| 2021/0189252 | A1 | 6/2021 | Timken |
| 2021/0189253 | A1 | 6/2021 | Timken |
| 2021/0189254 | A1 | 6/2021 | Timken |
| 2021/0301209 | A1 | 9/2021 | Timken |
| 2021/0301210 | A1 | 9/2021 | Timken |
| 2021/0332299 | A1 | 10/2021 | Timken |
| 2021/0332300 | A1 | 10/2021 | Timken |
| 2021/0363432 | A1 | 11/2021 | Bitting |
| 2022/0010211 | A1 | 1/2022 | Allegro, II |
| 2022/0010212 | A1 | 1/2022 | Shi |
| 2022/0010213 | A1 | 1/2022 | Sun |
| 2022/0010217 | A1 | 1/2022 | Barger |
| 2022/0010218 | A1 | 1/2022 | Davydov |
| 2022/0041905 | A1 | 2/2022 | Boaventura |
| 2022/0073826 | A1 | 3/2022 | Van Zijl |
| 2022/0089831 | A1 | 3/2022 | Kanattukara |
| 2022/0089957 | A1 | 3/2022 | Van Zijl |
| 2022/0089968 | A1 | 3/2022 | Driedger |
| 2022/0097279 | A1 | 3/2022 | Van Zijl |
| 2022/0098491 | A1 | 3/2022 | Abbott |
| 2022/0098497 | A1 | 3/2022 | Van Zijl |
| 2022/0135889 | A1 | 5/2022 | Van Zijl |
| 2022/0154078 | A1 | 5/2022 | Kann |

FOREIGN PATENT DOCUMENTS

| | | |
|---|---|---|
| EP | 0713906 B1 | 5/1999 |
| EP | 3744814 A1 | 12/2020 |
| EP | 3334804 B1 | 1/2021 |
| WO | 1995014069 A1 | 5/1995 |
| WO | 2005021686 A1 | 3/2005 |
| WO | 2014125344 A1 | 8/2014 |
| WO | 2015000840 A1 | 1/2015 |
| WO | 2015000842 A1 | 1/2015 |
| WO | 2015047085 A1 | 4/2015 |
| WO | 2017222380 A1 | 12/2017 |
| WO | 2018025103 A1 | 2/2018 |

(56) References Cited

FOREIGN PATENT DOCUMENTS

| | | |
|---|---|---|
| WO | 2018025104 A1 | 2/2018 |
| WO | 2018055555 A1 | 3/2018 |
| WO | 2018069794 A1 | 4/2018 |
| WO | 2018127812 A1 | 7/2018 |
| WO | 2018127813 A1 | 7/2018 |
| WO | 2018127817 A1 | 7/2018 |
| WO | 2020150244 A1 | 7/2020 |
| WO | 2020152317 A1 | 7/2020 |
| WO | 2020152319 A1 | 7/2020 |
| WO | 2020152320 A1 | 7/2020 |
| WO | 2020152327 A1 | 7/2020 |
| WO | 2020152329 A1 | 7/2020 |
| WO | 2020204707 A1 | 10/2020 |
| WO | 2020234679 A1 | 11/2020 |
| WO | 2020242912 A1 | 12/2020 |
| WO | 2020242914 A1 | 12/2020 |
| WO | 2020242916 A1 | 12/2020 |
| WO | 2020242917 A1 | 12/2020 |
| WO | 2020242918 A1 | 12/2020 |
| WO | 2020242920 A1 | 12/2020 |
| WO | 2020242925 A1 | 12/2020 |
| WO | 2020247192 A1 | 12/2020 |
| WO | 2020249853 A1 | 12/2020 |
| WO | 2020249854 A1 | 12/2020 |
| WO | 2020252228 A1 | 12/2020 |
| WO | 2021021849 A1 | 2/2021 |
| WO | 2021037851 A1 | 3/2021 |
| WO | 2021080898 A1 | 4/2021 |
| WO | 2021080899 A1 | 4/2021 |
| WO | 2021087023 A1 | 5/2021 |
| WO | 2021087026 A1 | 5/2021 |
| WO | 2021087028 A1 | 5/2021 |
| WO | 2021087032 A1 | 5/2021 |
| WO | 2021087052 A1 | 5/2021 |
| WO | 2021087059 A1 | 5/2021 |
| WO | 2021087062 A1 | 5/2021 |
| WO | 2021087066 A1 | 5/2021 |
| WO | 2021091724 A1 | 5/2021 |
| WO | 2021092288 A1 | 5/2021 |
| WO | 2021092306 A1 | 5/2021 |
| WO | 2021105326 A1 | 6/2021 |
| WO | 2021105327 A1 | 6/2021 |
| WO | 2021110395 A1 | 6/2021 |
| WO | 2021155407 A1 | 8/2021 |
| WO | 2021163106 A1 | 8/2021 |
| WO | 2021163109 A1 | 8/2021 |
| WO | 2021163111 A1 | 8/2021 |
| WO | 2021163113 A1 | 8/2021 |
| WO | 2021204818 A1 | 10/2021 |
| WO | 2021211517 A1 | 10/2021 |
| WO | 2021211523 A1 | 10/2021 |
| WO | 2021211529 A1 | 10/2021 |
| WO | 2021211537 A1 | 10/2021 |
| WO | 2021224287 A1 | 11/2021 |
| WO | 2021239699 A1 | 12/2021 |
| WO | 2021255591 A2 | 12/2021 |
| WO | 2022017894 A1 | 1/2022 |
| WO | 2022017897 A1 | 1/2022 |
| WO | 2022017899 A1 | 1/2022 |
| WO | 2022017901 A1 | 1/2022 |
| WO | 2022017902 A1 | 1/2022 |
| WO | 2022017903 A1 | 1/2022 |
| WO | 2022017904 A1 | 1/2022 |
| WO | 2022017906 A1 | 1/2022 |

OTHER PUBLICATIONS

"Cracking the Problem of Waste Plastic." ISCC Press Release dated Apr. 15, 2019. https://www.iscc-system.org/cracking-the-problem-of-waste-plastics/.

Ellen MacArthur Foundation and CE100 White Paper: Enabling a circular economy for chemicals with the mass balance approach. May 10, 2019.

GW Huber et al., The Chemistry and Kinetics of Polyethylene Pyrolysis: A Process to Produce Fuels and Chemicals, Chem Sus Chem, 13, 1764-1774, 2020.

International Search Report and Written Opinion for PCT/US2021/052411 dated Jan. 5, 2022. pp. 1-10.

Laermann, Michael, Chemical Recycling of Plastic Waste No More. Apr. 10, 2019.

Miandad, Rashid et al. Catalytic Pyrolysis of Plastic Waste: Moving Toward Pyrolysis Based Biorefineries. Frontiers in Energy Research. Mar. 19, 2019. vol. 7, Article 27.

Miskolczi, et al., "Fuels production by pyrolysis of waste plastics from agricultural and packaging sectors in a pilot scale reactor", Fuel Processing Technology (2009), 90(7-8), 1032-1040.

Mohammad Ali, et al., "The Conversion of Waste Plastics/Petroleum Residue Mixtures to Transportation Fuels", Chapter 14 in Feedstock Recycling and Pyrolysis of Waste Plastics (2006), 363-380.

Non-Final Office Action for U.S. Appl. No. 17/487,714 dated Jun. 1, 2022. pp. 1-11.

Non-Final Office Action for U.S. Appl. No. 17/487,770 dated Jun. 1, 2022. pp. 1-14.

Perspectives on Circular Economy in the Context of Chemical Engineering and Sustainable Development. Natalia A. Cano Londono and H. Cabezas, Chemical Engineering 2021, 34; 100738 www.sciencedirect.com (Years: 2021).

SABIC-Geleen ISCC PLUS Certificate. Certificate states that mass balance chain of custody is used. Date of issue Mar. 15, 2019.

SM Fakhrhoseini, Predicting Pyrolysis Products of PE, PP, and PET Using NRTL Activity Coefficient Model, Journal of Chemistry, 2013, 1-4.

Speight, J.G., 1999, The Chemistry and Technology of Petroleum, 3rd edition, Marcel Dekker, 918 pp.

International Search Report and Written Opinion for PCT/US2022/024433 dated Aug. 22, 2022. pp. 1-19.

PCT Partial Search Report for PCT8US2022/024433 dated Jun. 30, 2022. pp. 1-13.

* cited by examiner

PYROLYSIS OF PLASTIC WASTE TO PRODUCE LIGHT GASEOUS HYDROCARBONS AND INTEGRATION WITH AN ETHYLENE CRACKER

CROSS REFERENCE TO RELATED APPLICATIONS

This application claims the benefit of U.S. Provisional Patent Application No. 63/175,978, filed Apr. 16, 2021, which is incorporated herein by reference in its entirety.

TECHNICAL FIELD OF THE DISCLOSURE

This disclosure relates to the production of chemicals and plastics using pyrolysis products from the pyrolysis of plastic waste as a feedstock or co-feedstock with a petroleum-based or fossil fuel feed.

BACKGROUND OF THE DISCLOSURE

The worldwide environmental impact associated with discarded plastic waste products is substantial, and the incentive to recycle plastic wastes is pervasive. Feedstock recycling through the pyrolysis of plastic waste materials presents a potentially attractive alternative to conventional melt recycling of plastic wastes. Pyrolysis breaks down the polymeric components into hydrocarbon components, which then can be recycled in a refinery or chemical plant as a feedstock or co-feedstock and converted into fuels or chemicals.

One beneficial use of a pyrolysis product is to make ethylene, termed "circular" ethylene, which subsequently can be used to produce other circular products such as polyethylenes. Typically the desired product of pyrolysis is a mixture of liquids, but a preferred feedstock for ethylene and polyethylene production is a mixture of light hydrocarbon gases. However, it may be beneficial if pyrolysis systems could produce a high proportion of pyrolysis gas hydrocarbons versus pyrolysis oil or liquid hydrocarbons, thereby making it easier to integrate a pyrolysis process with an ethylene or polyethylene plant or with a natural gas or ethylene pipeline. Therefore, improved processes and systems for making and using pyrolysis gas and pyrolysis oil as feedstocks or co-feedstocks would be useful.

SUMMARY OF THE DISCLOSURE

This disclosure provides for new processes and methods for using pyrolysis gas and/or pyrolysis oil as a feedstock or co-feedstock for making, for example, circular ethylene, polyethylenes, and other circular products. Conventionally, pyrolysis reactors were typically optimized for pyrolysis oil production rather than pyrolysis gas, and the pyrolysis gas produced could be used as fuel for heating furnaces. However, pyrolysis gas is underutilized in this role, and by operating a pyrolysis unit under conditions selected to increase the proportion of pyrolysis gas relative to pyrolysis liquid in the pyrolysis unit effluent, various economic advantages may be achieved. In addition, the ability to adjust the pyrolysis unit operating conditions as a function of the relative economic value of the pyrolysis gas as a feed versus pyrolysis oil can provide additional economic advantages as described herein.

Generally pyrolysis of plastic waste has focused on producing pyrolysis oil which may be fed to a steam cracker where it is converted into ethylene and subsequently fed to a polyethylene reactor to produce circular polymers. These processes typically use pyrolysis conditions designed to enhance the production of liquid pyrolysis oil rather than gaseous pyrolysis products. However, most steam crackers that produce ethylene are designed to operate using light gaseous feeds, and the ability to feed liquid pyrolysis oil to a steam cracking furnace without disrupting the process is limited.

Therefore, in an aspect, this disclosure provides for pyrolyzing waste plastic under conditions which can enhance the production of $C_5$ and lighter gaseous hydrocarbon products relative to the proportion of light gases that are produced in conventional pyrolysis operations. These gaseous products can then be fed, for example, to a steam cracker furnace or mixed with the steam cracking furnace effluent, which is subsequently purified and fed to a polymerization reactor.

In one aspect, there is also provided a pyrolysis process which can convert plastic waste into $C_5$ and lighter hydrocarbon pyrolysis gases, which can be mixed with the effluent from a steam cracking furnace, purified or separated, and subsequently fed to a downstream reactor, for example, a polymerization reactor. In an aspect, any light saturated fractions such as ethane or propane which are produced during the purification/separation can be recycled to the steam cracking furnace.

In another aspect, there is provided a pyrolysis process which can convert plastic waste into $C_5$ and lighter hydrocarbon pyrolysis gases, which can undergo a condensation step to separate the heavier ($C_4$-$C_5$) products from the lighter ($C_2$-$C_3$) products in the pyrolysis gas stream. The lighter ($C_2$-$C_3$) gases can then be combined with the effluent from the steam cracking furnace and undergo a separation process downstream of the steam cracker furnace, subsequently sending ethylene and/or propylene to a downstream reactor or process of some type, for example, a polymerization reactor. The light saturated hydrocarbons can be recycled to the steam cracking furnace if desired. In this scenario, the heavier ($C_4$-$C_5$) products in the pyrolysis gas stream which would be condensed out can be fed to a steam cracking furnace as a feed or co-feed.

According to another aspect, there is provided a process which can convert plastic waste into $C_5$ and lighter hydrocarbon pyrolysis gas and a pyrolysis oil, in which the $C_5$ and lighter hydrocarbon gas stream, with or without the condensable components, can be fed downstream of a fluid catalytic cracker (FCC) to the FCC reactor effluent purification or separation unit.

In another aspect, the disclosure provides processes for producing a higher proportion of pyrolysis gas hydrocarbons versus pyrolysis oil hydrocarbons than conventional processes. According to aspects, the relative proportions of pyrolysis gas versus pyrolysis oil can be adjusted depending upon their respective market prices, which may enhance the economic viability of using pyrolysis products for producing chemicals and fuels.

In a further aspect, the polymers and chemicals of this disclosure can be certified in accordance with the International Sustainability and Carbon Certification (ISCC) provisions, as circular polymers and chemicals. Moreover, there are provided methods for certifying polymers and chemicals as circular at any point along complex chemical reaction pathways, even when remote from the point of introduction of the pyrolysis gas. The ability to trace the content of the polymer or chemicals to the original pyrolysis gas co-feedstock allows the ISCC certification to be made.

Therefore, among other things this disclosure describes the following Aspects I-VI.

I. In one aspect, this disclosure provides a process for recycling plastic waste, the process comprising:
  (a) pyrolyzing a plastic waste in a pyrolysis unit under a first set of pyrolysis conditions to produce a pyrolysis unit effluent comprising a pyrolysis gas and a pyrolysis oil in a known ratio and separating the pyrolysis gas from the pyrolysis oil, wherein the pyrolysis gas comprises $C_5$ and lighter ($C_1$, $C_2$, $C_3$, $C_4$, and $C_5$) hydrocarbons, including ethylene, propylene, and butylene (EPB);
  (b) feeding a first feed stream to a steam cracker furnace to produce a steam cracker furnace effluent comprising ethylene, propylene, and light ($C_2$-$C_3$) saturated hydrocarbons;
  (c) providing to a separation unit a separation unit feed comprising at least a portion of the pyrolysis gas and at least a portion of the steam cracker furnace effluent; and
  (d) separating the separation unit feed to provide circular products comprising an ethylene effluent, a propylene effluent, and a light ($C_2$-$C_3$) saturated hydrocarbon effluent.

II. In another aspect, there is provided a process for recycling plastic waste, the process comprising:
  (a) pyrolyzing a plastic waste in a pyrolysis unit under a first set of pyrolysis conditions to produce a pyrolysis unit effluent comprising a pyrolysis gas and a pyrolysis oil in a known ratio and separating the pyrolysis gas from the pyrolysis oil, wherein the pyrolysis gas comprises $C_5$ and lighter ($C_1$, $C_2$, $C_3$, $C_4$, and $C_5$) hydrocarbons, including ethylene, propylene, and butylene (EPB);
  (b) providing the pyrolysis gas to a condensing unit and forming a first condenser effluent having a higher proportion of $C_4$-$C_5$ hydrocarbons than the pyrolysis gas and a second condenser effluent having a higher proportion of $C_2$-$C_3$ hydrocarbons than the pyrolysis gas;
  (c) feeding a first feed stream to a steam cracker furnace to produce a steam cracker furnace effluent comprising ethylene, propylene, and light ($C_2$-$C_3$) saturated hydrocarbons;
  (d) providing to a separation unit a separation unit feed comprising at least a portion of the second condenser effluent and at least a portion of the steam cracker furnace effluent; and
  (e) separating the separation unit feed to provide circular products comprising an ethylene effluent, a propylene effluent, and a light ($C_2$-$C_3$) saturated hydrocarbon effluent.

III. There is also provided a process for recycling plastic waste according to any of Aspects I and II set out above, in which the process can further comprise the steps of:
  (a') assigning a market price to the pyrolysis oil formed under the first set of pyrolysis conditions as equivalent to a market price of a reference liquid product;
  (b') determining a market price of the combined ethylene, propylene, and butylene (EPB) in the pyrolysis gas formed under the first set of pyrolysis conditions; and
  (c') (1) when the market price of the combined EPB is greater than the market price of the pyrolysis oil, applying a second set of pyrolysis conditions which increase the proportion of pyrolysis gas relative to the pyrolysis oil in the pyrolysis reactor effluent; or (2) when the market price of the pyrolysis oil is greater than the market price of the combined EPB formed under the first set of conditions, applying a second set of pyrolysis conditions which increase the proportion of pyrolysis oil relative to the pyrolysis gas in the pyrolysis reactor effluent.

IV. In a further aspect, there is provided a process for recycling plastic waste, the process comprising:
  (a) pyrolyzing a plastic waste in a pyrolysis unit under a first set of pyrolysis conditions to produce a pyrolysis unit effluent comprising a pyrolysis gas and a pyrolysis oil in a known ratio and separating the pyrolysis gas from the pyrolysis oil, wherein the pyrolysis gas comprises $C_5$ and lighter ($C_1$, $C_2$, $C_3$, $C_4$, and $C_5$) hydrocarbons, including ethylene, propylene, and butylene (EPB);
  (b) assigning a market price to the pyrolysis oil formed under the first set of pyrolysis conditions as equivalent to a market price of a reference liquid product;
  (c) determining a market price of the combined ethylene, propylene, and butylene (EPB) in the pyrolysis gas formed under the first set of pyrolysis conditions; and
  (d) (1) when the market price of the combined EPB is greater than the market price of the pyrolysis oil, applying a second set of pyrolysis conditions which increase the proportion of pyrolysis gas relative to the pyrolysis oil in the pyrolysis reactor effluent; or (2) when the market price of the pyrolysis oil is greater than the market price of the combined EPB formed under the first set of conditions, applying a second set of pyrolysis conditions which increase the proportion of pyrolysis oil relative to the pyrolysis gas in the pyrolysis reactor effluent.

V. In a further aspect, the disclosure describes a process for recycling plastic waste, the process comprising:
  (a) pyrolyzing a plastic waste in a pyrolysis unit under a first set of pyrolysis conditions to produce a pyrolysis unit effluent comprising a pyrolysis gas and a pyrolysis oil in a known ratio and separating the pyrolysis gas from the pyrolysis oil, wherein the pyrolysis gas comprises $C_5$ and lighter ($C_1$, $C_2$, $C_3$, $C_4$, and $C_5$) hydrocarbons, including ethylene, propylene, and butylene (EPB);
  (b) feeding a first feed stream to a steam cracker furnace to produce a steam cracker furnace effluent comprising ethylene, propylene, and light ($C_2$-$C_3$) saturated hydrocarbons;
  (c) providing to a separation unit a separation unit feed comprising at least a portion of the pyrolysis gas and at least a portion of the steam cracker furnace effluent;
  (d) assigning a market price to the pyrolysis oil formed under the first set of pyrolysis conditions as equivalent to a market price of a reference liquid product;
  (e) determining a market price of the combined ethylene, propylene, and butylene (EPB) in the pyrolysis gas formed under the first set of pyrolysis conditions; and
  (f) (1) when the market price of the combined EPB is greater than the market price of the pyrolysis oil, applying a second set of pyrolysis conditions which increase the proportion of pyrolysis gas relative to the pyrolysis oil in the pyrolysis reactor effluent; or (2) when the market price of the pyrolysis oil is greater than the market price of the combined EPB formed under the first set of conditions, applying a second set of pyrolysis conditions which increase the proportion of pyrolysis oil relative to the pyrolysis gas in the pyrolysis reactor effluent.

VI. According to another aspect, there is provided a process for recycling plastic waste, the process comprising:

(a) pyrolyzing a plastic waste in a pyrolysis unit to produce a pyrolysis unit effluent comprising a pyrolysis gas and a pyrolysis oil and separating the pyrolysis gas from the pyrolysis oil, wherein the pyrolysis gas comprises $C_5$ and lighter ($C_{\leq 5}$) hydrocarbons having a $C_2$-$C_3$ fraction and a $C_4$-$C_5$ fraction;

(b) feeding a heavy hydrocarbon feed stream to a fluid catalytic cracker (FCC) reactor to produce an FCC effluent comprising naphtha ($C_6$-$C_{10}$ hydrocarbons) and $C_5$ and lighter ($C_{\leq 5}$) hydrocarbons;

(c) providing a fractionation unit feed comprising at least a portion of the pyrolysis gas and at least a portion of the FCC effluent to a fractionation unit; and (d) separating the fractionation unit feed to provide circular products comprising a first fractionation effluent comprising $C_5$ and lighter ($C_{\leq 5}$) hydrocarbons and a second fractionation effluent comprising heavy ($C_{6+}$) hydrocarbons.

Although pyrolysis reactors were traditionally optimized for pyrolysis oil production rather than pyrolysis gas, by operating a pyrolysis unit under conditions selected to increase, optimize, or maximize the proportion of pyrolysis gas relative to pyrolysis liquid in the pyrolysis unit effluent, one or more of the following advantages which make more beneficial use of pyrolysis gas than prior methods may be achieved. In one aspect, for example, when the ethylene effluent produced according to Aspect I or Aspect II above is fed to a polymerization reactor to form a circular polyethylene, the amount of circular polyethylene produced can be, for example, from about 10% greater to about 25% greater than the amount of circular polyethylene produced in a corresponding process that uses a liquid pyrolysis effluent feedstock only, as quantified by a percent (%) of gas yield from the pyrolysis unit per unit weight of plastic feed. In a further aspect, the carbon footprint of any independently selected circular product can be reduced by from about 15% to about 40% as compared to a carbon footprint a corresponding non-circular product produced in the absence of the pyrolysis gas and the pyrolysis oil. According to another aspect, the plastic waste can be pyrolyzed in an amount sufficient to displace up to about 10 wt % of a virgin feedstock required to produce the same amount of the ethylene effluent, the propylene effluent, and the light ($C_2$-$C_3$) saturated hydrocarbon effluent from a separation unit downstream of a steam cracker furnace. Further aspects provide that the plastic waste can be pyrolyzed in an amount sufficient to provide up to about 10 wt % of the separation unit feed.

These and other embodiments and aspects of the processes, methods, systems, and compositions are described more fully in the Detailed Description, the listed Aspects, and the claims and further disclosure such as the Examples provided herein.

BRIEF DESCRIPTION OF THE FIGURES

In FIG. 1, the pyrolysis gas is routed from the pyrolysis unit downstream of the steam cracker furnace, such that a separation unit feed receives as a feed both the steam cracker furnace effluent and the pyrolysis gas.

In FIG. 2, the pyrolysis gas is separated and the light portion ($C_2$-$C_3$ hydrocarbons) is routed downstream of the steam cracker furnace, such that a separation unit feed receives as a feed both the steam cracker furnace effluent and the light portion of the pyrolysis gas.

DETAILED DESCRIPTION OF THE DISCLOSURE

General Description

Figure 1:
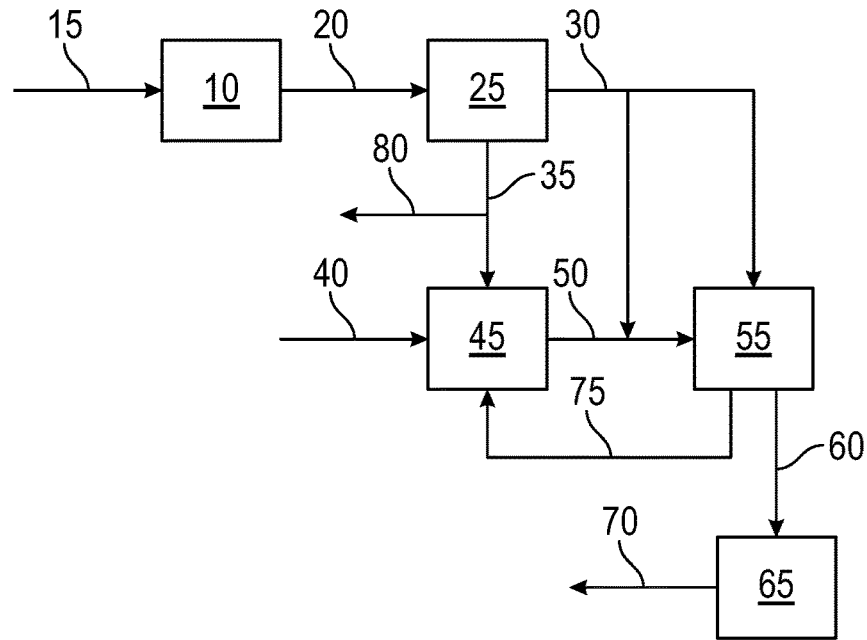
FIG. 1 illustrates a process for recycling plastic waste showing an exemplary process flowchart routing of feeds and products according to Aspect I.

Provided in this disclosure are processes and methods for using pyrolysis gas as a feedstock or a co-feedstock for making a variety of chemicals, for example, circular ethylene, polyethylenes, and other circular products. In these processes, pyrolysis reactor conditions can be adjusted to increase or optimize the production of pyrolysis gas over pyrolysis oil. Moreover, the operating parameters of a pyrolysis unit may be selected or adjusted to increase or decrease the proportion of pyrolysis gas relative to pyrolysis liquid in the pyrolysis unit effluent as a function of the relative economic value of the pyrolysis gas versus pyrolysis oil, which can enhance the economic viability of using pyrolysis products for producing chemicals and fuels.

Definitions

To define more clearly the terms used herein, the following definitions are provided, and unless otherwise indicated or the context requires otherwise, these definitions are applicable throughout this disclosure. If a term is used in this disclosure but is not specifically defined herein, the definition from the IUPAC Compendium of Chemical Terminology, $2^{nd}$ Ed (1997) can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Regarding claim transitional terms or phrases, the transitional term "comprising", which is synonymous with "including," "containing," or "characterized by," is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps and those that do not materially affect the basic and novel characteristic(s) of the claimed invention. A "consisting essentially of" claim occupies a middle ground between closed claims that are written in a "consisting of" format and fully open claims that are drafted in a "comprising" format. Unless specified to the contrary, describing a compound or composition "consisting essentially of" is not to be construed as "comprising," but is intended to describe the recited component that includes materials which do not significantly alter composition or method to which the term is applied. For example, a feedstock consisting essentially of a material A can include impurities typically present in a commercially produced or commercially available sample of the recited compound or composition. When a claim includes different features and/or feature classes (for example, a method step, feedstock features, and/or product features, among other possibilities), the transitional terms comprising, consisting essentially of, and consisting of, apply only to feature class to which is utilized and it is possible to have different transitional terms or phrases utilized with different features within a claim. For example a method can comprise several recited steps (and other non-recited steps) but utilize a catalyst composition preparation consisting of specific steps but utilize a catalyst composition comprising recited components and other non-recited components. While compositions and methods are described in terms of "comprising" various components or steps, the compositions and methods can also "consist essentially of" or "consist of" the various components or steps.

The terms "a," "an," and "the" are intended, unless specifically indicated otherwise, to include plural alternatives, e.g., at least one. For instance, the disclosure of "an organoaluminum compound" is meant to encompass one organoaluminum compound, or mixtures or combinations of more than one organoaluminum compound unless otherwise specified.

The terms "configured for use" or "adapted for use" and similar language is used herein to reflect that the particular recited structure or procedure is used in an olefin polymerization system or process. For example, unless otherwise specified, a particular structure "configured for use" means it is "configured for use in an olefin polymerization reactor system" and therefore is designed, shaped, arranged, constructed, and/or tailored to effect an olefin polymerization, as would have been understood by the skilled person.

For any particular compound disclosed herein, a general structure or name presented is also intended to encompass all structural isomers, conformational isomers, and stereoisomers that can arise from a particular set of substituents, unless indicated otherwise. Thus, a general reference to a compound includes all structural isomers unless explicitly indicated otherwise; e.g., a general reference to pentane includes n-pentane, 2-methyl-butane, and 2,2-dimethyl-propane, while a general reference to a butyl group includes an n-butyl group, a sec-butyl group, an iso-butyl group, and a tert-butyl group. Additionally, the reference to a general structure or name encompasses all enantiomers, diastereomers, and other optical isomers whether in enantiomeric or racemic forms, as well as mixtures of stereoisomers, as the context permits or requires. For any particular formula or name that is presented, any general formula or name presented also encompasses all conformational isomers, regioisomers, and stereoisomers that can arise from a particular set of substituents.

Unless otherwise specified, any carbon-containing group for which the number of carbon atoms is not specified can have, according to proper chemical practice, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 carbon atoms, or any range or combination of ranges between these values. For example, unless otherwise specified or unless the context requires otherwise, any carbon-containing group can have from 1 to 30 carbon atoms, from 1 to 25 carbon atoms, from 1 to 20 carbon atoms, from 1 to 15 carbon atoms, from 1 to 10 carbon atoms, or from 1 to 5 carbon atoms, and the like. In an aspect, the context could require other ranges or limitations, for example, when the subject carbon-containing group is an aryl group or an alkenyl group, the lower limit of carbons in these subject groups is six carbon atoms and two carbon atoms, respectively. Moreover, other identifiers or qualifying terms may be utilized to indicate the presence or absence of a particular substituent, a particular regiochemistry and/or stereochemistry, or the presence of absence of a branched underlying structure or backbone, and the like.

Various numerical ranges are disclosed herein. When Applicant discloses or claims a range of any type, Applicant's intent is to disclose or claim individually each possible number that such a range could reasonably encompass, including end points of the range as well as any sub-ranges and combinations of sub-ranges encompassed therein, unless otherwise specified. For example, by disclosing a temperature of from 70° C. to 80° C., Applicant's intent is to recite individually 70° C., 71° C., 72° C., 73° C., 74° C., 75° C., 76° C., 77° C., 78° C., 79° C., and 80° C., including any sub-ranges and combinations of sub-ranges encompassed therein, and these methods of describing such ranges are interchangeable. Moreover, all numerical end points of ranges disclosed herein are approximate, unless excluded by proviso. As a representative example, if Applicant states that one or more steps in the processes disclosed herein can be conducted at a temperature in a range from 10° C. to 75° C., this range should be interpreted as encompassing temperatures in a range from "about" 10° C. to "about" 75° C.

Values or ranges may be expressed herein as "about", from "about" one particular value, and/or to "about" another particular value. When such values or ranges are expressed, other embodiments disclosed include the specific value recited, from the one particular value, and/or to the other particular value. Similarly, when values are expressed as approximations, by use of the antecedent "about," it will be understood that the particular value forms another embodiment. It will be further understood that there are a number of values disclosed therein, and that each value is also herein disclosed as "about" that particular value in addition to the value itself. In another aspect, use of the term "about" means±15% of the stated value, ±10% of the stated value, ±5% of the stated value, or ±3% of the stated value.

Applicant reserves the right to proviso out or exclude any individual members of any such group of values or ranges, including any sub-ranges or combinations of sub-ranges within the group, that can be claimed according to a range or in any similar manner, if for any reason Applicant chooses to claim less than the full measure of the disclosure, for example, to account for a reference that Applicant may be unaware of at the time of the filing of the application. Further, Applicant reserves the right to proviso out or exclude any individual substituents, analogs, compounds, ligands, structures, or groups thereof, or any members of a claimed group, if for any reason Applicant chooses to claim less than the full measure of the disclosure, for example, to account for a reference or prior disclosure that Applicant may be unaware of at the time of the filing of the application.

The term "substituted" when used to describe a group, for example, when referring to a substituted analog of a particular group, is intended to describe any non-hydrogen moiety that formally replaces a hydrogen in that group, and is intended to be non-limiting. A group or groups can also be referred to herein as "unsubstituted" or by equivalent terms such as "non-substituted," which refers to the original group in which a non-hydrogen moiety does not replace a hydrogen within that group. Unless otherwise specified, "substituted" is intended to be non-limiting and include inorganic substituents or organic substituents as understood by one of ordinary skill in the art.

An "aliphatic" compound is a class of acyclic or cyclic, saturated or unsaturated, carbon compounds, excluding aromatic compounds, e.g., an aliphatic compound is a non-aromatic organic compound. An "aliphatic group" is a generalized group formed by removing one or more hydrogen atoms (as necessary for the particular group) from a carbon atom of an aliphatic compound. Aliphatic compounds and therefore aliphatic groups can contain organic functional group(s) and/or atom(s) other than carbon and hydrogen.

The term "alkene" whenever used in this specification and claims refers to an olefin that has at least one carbon-carbon double bond. The term "alkene" includes aliphatic or aromatic, cyclic or acyclic, and/or linear and branched alkene unless expressly stated otherwise. The term "alkene," by itself, does not indicate the presence or absence of heteroatoms and/or the presence or absence of other carbon-carbon double bonds unless explicitly indicated. Other identifiers may be utilized to indicate the presence or absence of particular groups within an alkene. Alkenes may also be further identified by the position of the carbon-carbon double bond. Alkenes, having more than one such multiple bond are alkadienes, alkatrienes, and so forth, and may be further identified by the position of the carbon-carbon double bond.

The term "olefin" is used herein in accordance with the definition specified by IUPAC: acyclic and cyclic hydrocarbons having one or more carbon-carbon double bonds apart from the formal ones in aromatic compounds. The class "olefins" subsumes alkenes and cycloalkenes and the corresponding polyenes. Ethylene, propylene, 1-butene, 2-butene, 1-hexene and the like are non-limiting examples of olefins. The term "alpha olefin" as used in this specification and claims refers to an olefin that has a double bond between the first and second carbon atom of the longest contiguous chain of carbon atoms. The term "alpha olefin" includes linear and branched alpha olefins unless expressly stated otherwise.

An "aromatic group" refers to a generalized group formed by removing one or more hydrogen atoms (as necessary for the particular group and at least one of which is an aromatic ring carbon atom) from an aromatic compound. Thus, an "aromatic group" as used herein refers to a group derived by removing one or more hydrogen atoms from an aromatic compound, that is, a compound containing a cyclically conjugated hydrocarbon that follows the Hückel (4n+2) rule and containing (4n+2) pi-electrons, where n is an integer from 1 to about 5. Aromatic compounds and hence "aromatic groups" may be monocyclic or polycyclic unless otherwise specified. Aromatic compounds include "arenes" (hydrocarbon aromatic compounds) and "heteroarenes," also termed "hetarenes" (heteroaromatic compounds formally derived from arenes by replacement of one or more methine (—C═) carbon atoms by trivalent or divalent heteroatoms, in such a way as to maintain the continuous pi-electron system characteristic of aromatic systems and a number of out-of-plane pi-electrons corresponding to the Hückel rule (4n+2)). While arene compounds and heteroarene compounds are mutually exclusive members of the group of aromatic compounds, a compound that has both an arene group and a heteroarene group that compound generally is considered a heteroarene compound. Aromatic compounds, arenes, and heteroarenes may be mono- or polycyclic unless otherwise specified. Examples of arenes include, but are not limited to, benzene, naphthalene, and toluene, among others. Examples of heteroarenes include, but are not limited to furan, pyridine, and methylpyridine, among others. As disclosed herein, the term "substituted" may be used to describe an aromatic group wherein any non-hydrogen moiety formally replaces a hydrogen in that group, and is intended to be non-limiting.

The term "polymer" is used herein generically to include olefin homopolymers, copolymers, terpolymers, and so forth. A copolymer is derived from an olefin monomer and one olefin comonomer, while a terpolymer is derived from an olefin monomer and two olefin comonomers. Accordingly, "polymer" encompasses copolymers, terpolymers, etc., derived from any olefin monomer and comonomer(s) disclosed herein. Similarly, an ethylene polymer would include ethylene homopolymers, ethylene copolymers, ethylene terpolymers, and the like. As an example, an olefin copolymer, such as an ethylene copolymer, can be derived from ethylene and a comonomer, such as 1-butene, 1-hexene, or 1-octene. If the monomer and comonomer were ethylene and 1-hexene, respectively, the resulting polymer could be categorized an as ethylene/1-hexene copolymer.

In like manner, the scope of the term "polymerization" includes homopolymerization, copolymerization, terpolymerization, etc. Therefore, a copolymerization process could involve contacting one olefin monomer (e.g., ethylene) and one olefin comonomer (e.g., 1-hexene) to produce a copolymer.

The term "cracker" is used herein to refer to a stream cracking unit or a fluid catalytic cracking (FCC) unit. Thus, unless otherwise specified, the steam cracking unit comprises a steam cracking furnace into which a pyrolysis product may be fed, upstream pretreatment equipment, and downstream separations equipment. The FCC comprises a fluid catalytic cracking reactor, an upstream pretreater, and downstream separations equipment. Pyrolysis oil is usually fed to the FCC pretreater, although the pyrolysis oil may also be fed to the FCC reactor directly.

The terms "reforming", "reformer" or "reforming unit" are used herein, and the terms "Aromax" or "AROMAX®" unit are also used. While both reforming units and Aromax units make aromatics, there is a difference in the catalysts used in these units. However the methods and processes disclosed herein can be used with either a reforming unit or an Aromax unit, and for the purposes of this disclosure, it should be considered that when one type unit is specified, the other type of unit may also be used and is to be considered disclosed. The reforming catalysts are alumina-based and contain a metal such as platinum. The Aromax catalyst is a zeolite-based catalyst and also contains platinum or other group VIII or 1B metals (Groups 8-11 metals) and a halide such as chloride, fluoride, and the like. Both processes feed naphtha from fluid catalytic cracking (FCC) unit. However, because of the sulfur hydrotreater just upstream of the Aromax unit, it is also possible to feed pyrolysis oil directly to the sulfur hydrotreater, bypassing the FCC unit.

When referring to "natural gas" feed in this disclosure, it is intended to refer to a Natural Gas Liquids (NGL) feed. Thus, the petroleum/fossil fuel feed to the steam cracker/steam cracking furnace can be a light hydrocarbon, mostly saturated feed ranging from $C_2$-$C_5$ (following methane removal), and the steam cracking furnace primarily feeds a mix of $C_2$-$C_3$. A Natural Gas Liquids (NGL) facility separates out the methane, and in some cases, the purified $C_2$-$C_3$ feed. Alternatively, the steam cracking furnace could also feed naphtha ($C_6$-$C_{10}$), and the steam cracker that feeds naphtha may also mix in pyrolysis oil with the naphtha feed.

Although any methods, devices, and materials similar or equivalent to those described herein can be used in the practice or testing of the invention, the typical methods, devices and materials are herein described.

All publications and patents mentioned herein are incorporated herein by reference for the purpose of describing and disclosing, for example, the constructs and methodologies that are described in the publications, which might be used in connection with the presently described invention.

The publications discussed throughout the text are provided solely for their disclosure prior to the filing date of the present application. Nothing herein is to be construed as an admission that the inventors are not entitled to antedate such disclosure by virtue of prior invention.

Pyrolysis of Plastic Waste to Produce Light Gaseous Hydrocarbons and Integration of a Pyrolysis Unit with an Ethylene Cracker. Regarding Aspect I of this disclosure, there is provided a process for recycling plastic waste which includes producing chemicals or polymers from plastic waste, the process comprising:

(a) pyrolyzing a plastic waste in a pyrolysis unit under a first set of pyrolysis conditions to produce a pyrolysis unit effluent comprising a pyrolysis gas and a pyrolysis oil in a known ratio, wherein the pyrolysis gas comprises $C_5$ and lighter ($C_1$, $C_2$, $C_3$, $C_4$, and $C_5$) hydrocarbons, including ethylene, propylene, and butylene (EPB);

(b) feeding a first feed stream to a steam cracker furnace to produce a steam cracker furnace effluent comprising ethylene, propylene, and light ($C_2$-$C_3$) saturated hydrocarbons;

(c) providing to a separation unit a separation unit feed comprising at least a portion of the pyrolysis gas and at least a portion of the steam cracker furnace effluent; and (d) separating the separation unit feed to provide circular products comprising an ethylene effluent, a propylene effluent, and a light ($C_2$-$C_3$) saturated hydrocarbon effluent.

In this aspect, the pyrolysis gas is routed downstream of the steam cracker to the separation unit and the ethylene, propylene, light ($C_2$-$C_3$) saturated hydrocarbons, and other effluents can be subsequently routed from the separation unit. The pyrolysis gas and the steam cracker furnace effluent can be combined to form the separation unit feed of desired, or pyrolysis gas and the steam cracker furnace effluent can be provided to the separation unit separately. In either aspect, the separation unit feed can comprise at least a portion of the pyrolysis gas and at least a portion of the steam cracker furnace effluent. If desired, the pyrolysis gas can be compressed prior to providing at least a portion of the pyrolysis gas as a separation unit feed to the separation unit.

According to Aspect II of this disclosure, there is provided a process for recycling plastic waste which includes producing chemicals or polymers from plastic waste, the process comprising:

(a) pyrolyzing a plastic waste in a pyrolysis unit under a first set of pyrolysis conditions to produce a pyrolysis unit effluent comprising a pyrolysis gas and a pyrolysis oil, wherein the pyrolysis gas comprises $C_5$ and lighter ($C_1$, $C_2$, $C_3$, $C_4$, and $C_5$) hydrocarbons, including ethylene, propylene, and butylene (EPB);

(b) providing the pyrolysis gas to a condensing unit and forming a first condenser effluent having a higher proportion of $C_4$-$C_5$ hydrocarbons than the pyrolysis gas and a second condenser effluent having a higher proportion of $C_2$-$C_3$ hydrocarbons than the pyrolysis gas;

(c) feeding a first feed stream to a steam cracker furnace to produce a steam cracker furnace effluent comprising ethylene, propylene, and light ($C_2$-$C_3$) saturated hydrocarbons;

(d) providing to a separation unit a separation unit feed comprising at least a portion of the second condenser effluent and at least a portion of the steam cracker furnace effluent; and (e) separating the separation unit feed to provide circular products comprising an ethylene effluent, a propylene effluent, and a light ($C_2$-$C_3$) saturated hydrocarbon effluent.

In this aspect, the second condenser effluent and the steam cracker furnace effluent can be combined prior to step (d) to form the separation unit feed. This aspect can further comprise the step of feeding at least a portion of the first condenser effluent to the steam cracker furnace. If desired, the first condenser effluent and the first feed stream can be combined prior to feeding to the steam cracking furnace or they can be provided to the steam cracking furnace separately.

Once the separation unit feed is separated to provide circular products comprising an ethylene effluent, a propylene effluent, and a light ($C_2$-$C_3$) saturated hydrocarbon effluent according to Aspect I or Aspect II, the light saturated hydrocarbon effluent or a portion thereof can be recycling to the steam cracking furnace for further production of ethylene. The light saturated hydrocarbon effluent or the portion thereof can be treated to remove contaminants prior to recycling to the steam cracking furnace.

The feed stream to the steam cracker furnace which produces a steam cracker furnace effluent is described herein as the first feed stream, which can comprise Liquefied Petroleum Gas (LPG), Natural Gas Liquids (NGL), light ($C_2$-$C_5$) hydrocarbons, or naphtha ($C_6$-$C_{10}$) and the like. In addition, the feed stream to the steam cracker furnace can also comprise the pyrolysis oil or a portion thereof which can be fed from the pyrolysis unit to the steam cracker furnace. For example, in one aspect, the steam cracker feed (the first feed stream) can comprise a combination of naphtha ($C_6$-$C_{10}$) or any other of the first feed stream components or combinations thereof, along with the pyrolysis oil or a portion thereof which is produced in the pyrolysis unit.

In one aspect of the disclosed process for recycling plastic waste, the first feed stream to the steam cracker can comprise paraffins or paraffins along with olefins. In this aspect, at least a portion of the olefins can be removed from the first feed stream prior to feeding the first feed stream to the steam cracker furnace. For example, the olefins can be removed from the first feed stream by contacting the first feed stream with sulfolane or by other methods as understood by the person of skill in the art.

In another aspect, the pyrolysis oil from the pyrolysis unit can be recycled to a refinery unit as a feedstock or co-feedstock. For example, the pyrolysis oil can be recycled to refinery crude unit to produce circular naphtha or circular natural gas liquids (NGL).

In order to use the pyrolysis gas from the pyrolysis unit as disclosed herein, it is advantageous to co-locate the pyrolysis unit with the steam cracker furnace. In another aspect, it is advantageous to co-locate the pyrolysis unit with the separation unit described above, or alternatively, to co-locate the pyrolysis unit with both the steam cracker furnace and the separation unit as described above. By describing these units as co-located, it is intended to indicate that the pyrolysis unit is located sufficiently close to the steam cracker furnace or the separation unit that the pyrolysis unit, the steam cracker furnace, and/or the separation unit are co-located on the same unit plot space within the same operating crew. For example, the pyrolysis unit can be located sufficiently close to the steam cracker furnace or the separation unit or both that the $C_2$-$C_3$ fraction of the pyrolysis gas or the second condenser effluent can be supplied to the steam cracker furnace without additional compression or a pipeline. In one aspect, the $C_2$-$C_3$ fraction of the pyrolysis gas or the second condenser effluent can be transported via pipeline to the steam cracker furnace and are not compressed. In another aspect, whether the pyrolysis unit, the steam cracker furnace, and/or the separation unit are co-located or not co-located, the $C_2$-$C_3$ fraction of the pyrolysis gas or the second condenser effluent can be compressed and transported via pipeline to the steam cracker furnace.

FIG. 1 illustrates a process for recycling plastic waste showing an exemplary process flowchart routing of feeds and products, for example, a process according to Aspect I. Illustrated in FIG. 1 are a pyrolysis unit 10 which can include a pyrolysis furnace or reactor and which can accept a variety of plastic waste products as a pyrolysis unit feed 15. The pyrolysis unit feed 15 is pyrolyzed in pyrolysis unit 10 to form a pyrolysis unit effluent 20 which, followed by separation at 25, which provides a pyrolysis gas 30 and a pyrolysis oil 35. The pyrolysis gas for example, can comprise $C_1$ to $C_5$ hydrocarbons, including ethylene, propylene, and butylene (EPB).

The FIG. 1 process also illustrates a first feed stream 40 which is fed to a steam cracker furnace 45 to produce a steam cracker furnace effluent 50 which can comprise, for example, olefins such as ethylene and propylene, and light ($C_2$-$C_3$) saturated hydrocarbons. Steam cracker furnace effluent 50 is fed to a separation unit 55 downstream of the steam cracker furnace 45, and the pyrolysis gas 30 is routed downstream of the steam cracker furnace 45. Therefore, separation unit 55 receives as a feed both the steam cracker furnace effluent 50 and the pyrolysis gas 30. The pyrolysis gas 30 can be fed either directly to separation unit 55 or combined with the steam cracker furnace effluent 50 prior to feeding to separation unit 55, as illustrated.

The separation unit feed then can be separated to form various effluents from the separation unit 55, such as an olefin effluents 60. For example olefin effluents 60 can be an ethylene effluent, which subsequently can be fed to a polymerization reactor 65 to form polyethylene 70. The separation unit 55 downstream of the steam cracker furnace 45 can also provide a light ($C_2$-$C_3$) saturated hydrocarbon effluent 75 which, if desired, can be recycled to the steam cracker furnace 45.

The pyrolysis oil 35 produced according to FIG. 1 can be routed to other uses such as a refinery 80 or, if desired, the pyrolysis oil 35 can be used as a feed or co-feed for a stream cracking furnace 45.

Figure 2:
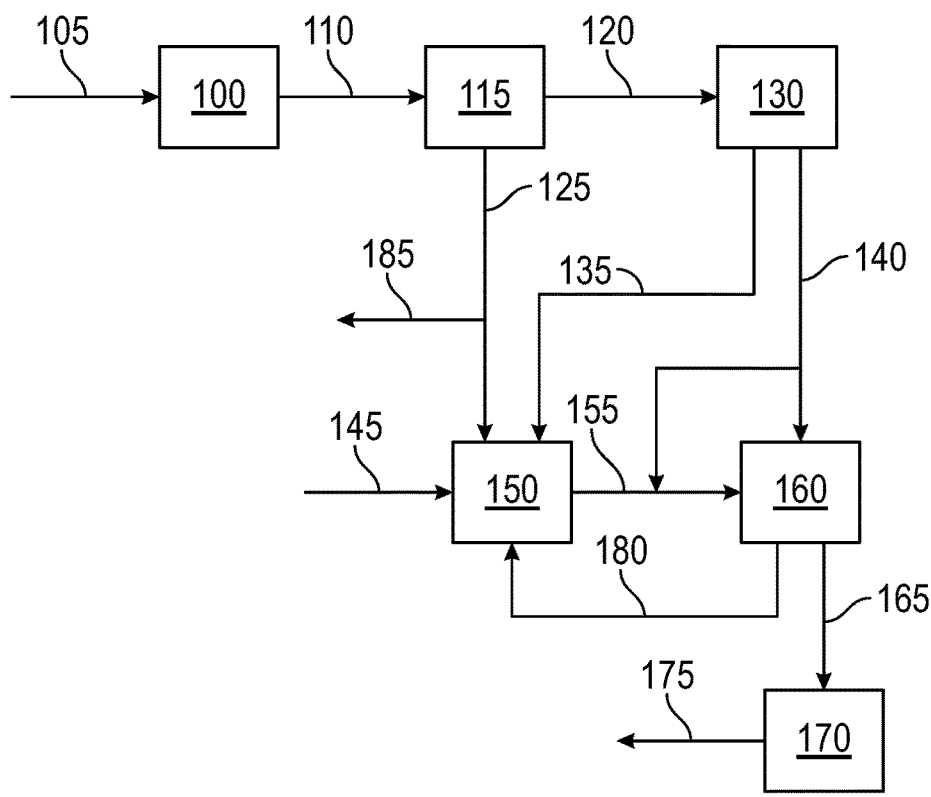
FIG. 2 illustrates another process for recycling plastic waste showing an exemplary process flowchart routing of feeds and products according to Aspect II.

FIG. 2 illustrates another process for recycling plastic waste showing an exemplary process flowchart routing of feeds and products according to Aspect II. In FIG. 2, pyrolysis unit 100 is shown which can include a pyrolysis furnace or reactor and which can accept a variety of plastic waste products as the pyrolysis unit feed 105. The pyrolysis unit feed 105 is pyrolyzed in pyrolysis unit 100 to form a pyrolysis unit effluent 110 which, followed by separation at 115, provides a pyrolysis gas 120 and a pyrolysis oil 125. The pyrolysis gas for example, can comprise $C_1$ to $C_5$ hydrocarbons, including ethylene, propylene, and butylene (EPB). Pyrolysis gas 120 is subsequently routed to a condensing unit 130 which can form a first condenser effluent 135 having a higher proportion of $C_4$-$C_5$ hydrocarbons than the pyrolysis gas and a second condenser effluent 140 having a higher proportion of $C_2$-$C_3$ hydrocarbons than the pyrolysis gas.

The FIG. 2 process also illustrates a first feed stream 145 which is fed to a steam cracker furnace 150 to produce a steam cracker furnace effluent 155 which can comprise, for example, olefins such as ethylene and propylene, and light ($C_2$-$C_3$) saturated hydrocarbons. Steam cracker furnace effluent 155 is then fed to a separation unit 160 downstream of the steam cracker furnace 150, and the second condenser effluent 140 is routed downstream of the steam cracker furnace 150. Therefore, separation unit 160 receives as a feed both the steam cracker furnace effluent 155 and the lighter portion of the pyrolysis gas, which is the second condenser effluent 140 having a higher concentration of $C_2$-$C_3$ hydrocarbons than the pyrolysis gas. The second condenser effluent 140 can be fed either directly to separation unit 160 or combined with the steam cracker furnace effluent 155 prior to feeding to separation unit 160, as illustrated. The first condenser effluent 135 having a higher proportion of $C_4$-$C_5$ hydrocarbons than the pyrolysis gas 120 can be routed to the steam cracker furnace 150. The first condenser effluent 135 can be fed directly to the steam cracker furnace 150 or, if desired, combined with the first feed stream prior to feeding to the steam cracker furnace 150.

The separation unit feed which includes both the steam cracker furnace effluent 155 and the second condenser effluent 140 may then be separated to form various effluents from the separation unit 160, such as an olefin effluents 165. For example olefin effluents 165 can be an ethylene effluent, which subsequently can be fed to a polymerization reactor 170 to form polyethylene 175. The separation unit 160 downstream of the steam cracker furnace 150 can also provide a light ($C_2$-$C_3$) saturated hydrocarbon effluent 180 which, if desired, can be recycled to the steam cracker furnace 150. The pyrolysis oil 125 produced according to FIG. 2 can be routed to other uses such as a refinery 185 or, if desired, the pyrolysis oil 125 can be used as a feed or co-feed for a stream cracking furnace 150.

In the FIG. 1 and the FIG. 2 embodiments, the process for recycling plastic waste as described can further include the steps of utilizing an economic decision tree to adjust the operation of the pyrolysis unit from a first set of conditions to a new second set of conditions, which either increases or decreases the proportion of pyrolysis gas relative to the proportion of pyrolysis oil in the pyrolysis unit effluent. This economic decision process is based upon the relative market prices of the products produced under the first set of conditions and whether the second set of conditions should be selected to increase or decrease the proportion of pyrolysis gas relative to pyrolysis oil as disclosed hereinbelow.

Economic Analysis Applied to the Pyrolysis of Plastic Waste. This disclosure also provides for a process of recycling plastic waste which involves determining and setting or adjusting the operating parameters of the pyrolysis unit to either enhance the production of pyrolysis gas or to enhance the production of pyrolysis oil or liquids. In particular, it has been discovered that by operating a pyrolysis unit under conditions selected to increase the proportion of pyrolysis gas relative to pyrolysis liquid in the pyrolysis unit effluent, various economic advantages may be achieved.

In accordance with Aspect III of this disclosure, there is provided a process for recycling plastic waste according to either of Aspect I or Aspect II, in which Aspect III further comprises the steps of:

(a') assigning a market price to the pyrolysis oil formed under the first set of pyrolysis conditions as equivalent to a market price of a reference liquid product;

(b') determining a market price of the combined ethylene, propylene, and butylene (EPB) in the pyrolysis gas formed under the first set of pyrolysis conditions; and (c') (1) when the market price of the combined EPB is greater than the market price of the pyrolysis oil, applying a second set of pyrolysis conditions which increase the proportion of pyrolysis gas relative to the pyrolysis oil in the pyrolysis reactor effluent; or (2) when the market price of the pyrolysis oil is greater than the market price of the combined EPB formed under the first set of conditions, applying a second set of pyrolysis conditions which increase the proportion of pyrolysis oil relative to the pyrolysis gas in the pyrolysis reactor effluent.

Different methods for valuation of the pyrolysis gas products and the pyrolysis oil products can be used. For example, market prices of the combined ethylene, propylene, and butylene (EPB) products in the pyrolysis gas can be compared with an assigned market price of the pyrolysis oil, each of which are formed under the first set of pyrolysis conditions. Assigning a market price to the pyrolysis oil can be accomplished in various ways, for example, assigning a market price to each distillation cut in the pyrolysis oil as equal to a market price of an equivalent reference liquid product for each distillation cut.

It is not necessary that the economic analysis be applied to the pyrolysis of plastic waste only when carried out according to Aspect I and Aspect II. For example, this disclosure also provides according to Aspect IV, a process for recycling plastic waste in which the process comprises the steps of:

(a) pyrolyzing a plastic waste in a pyrolysis unit under a first set of pyrolysis conditions to produce a pyrolysis unit effluent comprising a pyrolysis gas and a pyrolysis oil in a known ratio, wherein the pyrolysis gas comprises $C_5$ and lighter ($C_1$, $C_2$, $C_3$, $C_4$, and $C_5$) hydrocarbons, including ethylene, propylene, and butylene (EPB);

(b) assigning a market price to the pyrolysis oil formed under the first set of pyrolysis conditions as equivalent to a market price of a reference liquid product;

(c) determining a market price of the combined ethylene, propylene, and butylene (EPB) in the pyrolysis gas formed under the first set of pyrolysis conditions; and (d) (1) when the market price of the combined EPB is greater than the market price of the pyrolysis oil, applying a second set of pyrolysis conditions which increase the proportion of pyrolysis gas relative to the pyrolysis oil in the pyrolysis reactor effluent; or (2) when the market price of the pyrolysis oil is greater than the market price of the combined EPB formed under the first set of conditions, applying a second set of pyrolysis conditions which increase the proportion of pyrolysis oil relative to the pyrolysis gas in the pyrolysis reactor effluent.

The methods for valuation of the pyrolysis gas products and the pyrolysis oil products that can be used in the other aspects can also be used in this aspect or embodiment.

In another aspect of the disclosure the economic analysis and resulting response thereto can be applied to the pyrolysis of plastic waste separate from Aspect I and Aspect II in accordance with Aspect V, which provides a process for recycling plastic waste in which the process comprises the steps of:

(a) pyrolyzing a plastic waste in a pyrolysis unit under a first set of pyrolysis conditions to produce a pyrolysis unit effluent comprising a pyrolysis gas and a pyrolysis oil in a known ratio, wherein the pyrolysis gas comprises $C_5$ and lighter ($C_1$, $C_2$, $C_3$, $C_4$, and $C_5$) hydrocarbons, including ethylene, propylene, and butylene (EPB);

(b) feeding a first feed stream to a steam cracker furnace to produce a steam cracker furnace effluent comprising ethylene, propylene, and light ($C_2$-$C_3$) saturated hydrocarbons;

(c) providing to a separation unit a separation unit feed comprising at least a portion of the pyrolysis gas and at least a portion of the steam cracker furnace effluent;

(d) assigning a market price to the pyrolysis oil formed under the first set of pyrolysis conditions as equivalent to a market price of a reference liquid product;

(e) determining a market price of the combined ethylene, propylene, and butylene (EPB) in the pyrolysis gas formed under the first set of pyrolysis conditions; and (f) (1) when the market price of the combined EPB is greater than the market price of the pyrolysis oil, applying a second set of pyrolysis conditions which increase the proportion of pyrolysis gas relative to the pyrolysis oil in the pyrolysis reactor effluent; or (2) when the market price of the pyrolysis oil is greater than the market price of the combined EPB formed under the first set of conditions, applying a second set of pyrolysis conditions which increase the proportion of pyrolysis oil relative to the pyrolysis gas in the pyrolysis reactor effluent.

The methods for valuation of the pyrolysis gas products and the pyrolysis oil products that can be used in the other aspects may also be used in this aspect or embodiment.

As described above, different methods for assigning of determining the market prices or valuation of the pyrolysis gas products and the pyrolysis oil products can be used. For example, the pyrolysis gas can be valued by determining the market prices of valuable components of the pyrolysis gas, for example the combined ethylene, propylene, and butylene (EPB) in the pyrolysis gas. This value then may be compared with an assigned market price of the pyrolysis oil, formed under the same original set of pyrolysis conditions used to form the pyrolysis gas. In one aspect, the disclosed processes can further include the step of tracking the market price of the combined EPB and the market price of the reference liquid product in real time.

Assigning a market price to the pyrolysis oil can be accomplished in various ways. For example, a market price can be assigned to each distillation cut in the pyrolysis oil as equal to a market price of an equivalent reference liquid product for each of the distillation cuts. In this aspect, the market price assigned to the pyrolysis oil can be a weighted average of the equivalent reference liquid product for each distillation cut, as a function of the amount of each distillation cut obtained from the pyrolysis oil. For example, the distillation cuts of the pyrolysis oil can comprise any combination of distillation cuts selected from diesel, gasoline, naphtha, kerosene, gas oil, and waxes.

In another aspect, when assigning a market price to the pyrolysis oil, the reference liquid product can comprise gasoline, diesel, or a blend of gasoline and diesel. For example, the reference liquid product can comprise a blend of gasoline and diesel having about 95 wt % to 5 wt % gasoline and about 5 wt % to 95 wt % diesel. That is, if desired the reference liquid product can be adjusted a function of the properties of the pyrolysis oil such as the properties and quantities of the distillation cuts obtained from pyrolysis oil. In another aspect, the reference liquid product can include a blend of gasoline and diesel having about 90 wt % to 50 wt % gasoline and about 10 wt % to 50 wt % diesel. Alternatively, the reference liquid product can include a blend of gasoline and diesel having about 70 wt % gasoline and about 30 wt % diesel.

When the relative market prices are determined for the pyrolysis gas and for the pyrolysis oil formed under the first set of pyrolysis conditions, these prices can be compared to determine whether the market conditions can provide greater overall margins by increasing the relative amount of pyrolysis gas in the pyrolysis unit effluent, or by increasing the relative amount of pyrolysis oil in the pyrolysis unit effluent. Once determined, a second set of pyrolysis conditions can be applied which either increases the proportion of pyrolysis gas relative to the pyrolysis oil in the pyrolysis unit effluent or increases the proportion of pyrolysis oil relative to the pyrolysis gas in the pyrolysis unit effluent. In an aspect, applying the second set of pyrolysis conditions increases the proportion of pyrolysis gas relative to the pyrolysis oil in the pyrolysis reactor effluent. In another aspect, applying the second set of pyrolysis conditions increases the proportion of pyrolysis oil relative to the pyrolysis gas in the pyrolysis reactor effluent.

According to an aspect, upon applying the second set of pyrolysis conditions, a pyrolysis reactor effluent having from about 60 wt % to about 85 wt % pyrolysis gas, and having from about 40 wt % to about 15 wt % pyrolysis liquid can be obtained. Alternatively, upon applying the second set of pyrolysis conditions, a pyrolysis reactor effluent can be formed which has from about 75 wt % to about 83 wt % pyrolysis gas, and having from about 25 wt % to about 17 wt % pyrolysis liquid.

In a further aspect, applying the second set of pyrolysis conditions may increase the proportion of pyrolysis gas relative to the pyrolysis oil in the pyrolysis reactor effluent, wherein the pyrolysis oil produced under the second set of pyrolysis conditions has a higher aromatic content than that of the pyrolysis oil produced under the second set of pyrolysis conditions. Applying the second set of pyrolysis conditions may also increases the proportion of pyrolysis gas relative to the pyrolysis oil in the pyrolysis reactor effluent, wherein the pyrolysis oil produced under the second set of pyrolysis conditions has a lower wax content than that of the pyrolysis oil produced under the second set of pyrolysis conditions.

In each of these processes for recycling plastic waste using pyrolysis gas, pyrolysis oil, or both, the weight or fraction of the circular products which is attributable to the pyrolysis gas or plastic waste can be determined by mass balance, examples of which are provided herein. The disclosed processes can further include the step of certifying the pyrolysis oil, the pyrolysis gas, or any subsequent product produced using the pyrolysis oil or the pyrolysis gas as circular in accordance with International Sustainability and Carbon Certification (ISCC) standards, based upon the weight or fraction of the circular product attributable to the plastic waste, as determined by mass balance and the free attribution method.

Pyrolysis Unit Operation, Pyrolysis Gas, and Pyrolysis Oil. Conventional pyrolysis reactors have been operated to favor the production of pyrolysis oil for use in chemical and refinery processes, with the less desirable pyrolysis gas often used as a fuel. Applicant has discovered that by operating a pyrolysis unit under conditions selected to increase the proportion of pyrolysis gas relative to pyrolysis oil in the pyrolysis unit effluent, various economic advantages may be achieved. This disclosure also provides for adjusting the pyrolysis unit operating conditions as a function of the relative economic value of the pyrolysis gas as a feed versus pyrolysis oil to provide additional economic advantages.

The skilled artisan will understand conventional pyrolysis unit operations to favor the production of pyrolysis oil. In an aspect, the pyrolysis unit can be operated under conditions selected to increase, optimize, or maximize the proportion of pyrolysis gas in the pyrolysis unit effluent relative to pyrolysis liquid (also termed pyrolysis oil) in the pyrolysis unit effluent. For example, pyrolysis temperatures, the use and selection of catalysts, and the like, can be employed to increase the relative proportion of pyrolysis gas versus pyrolysis oil. The person of skill will appreciate the pyrolysis parameters that can be regulated in order to increase the yield of gas-phase products in a pyrolysis unit. For example, the publications: (1) G. W. Huber et al., The Chemistry and Kinetics of Polyethylene Pyrolysis: A Process to Produce Fuels and Chemicals, *ChemSusChem* 2020, 13, 1764-1774; and (2) S. M. FakhrHoseini and M. Dastanian, J. Chem. 2013, 1-5, describe the influence of pyrolysis conditions, including temperature, reactor type, residence time, catalyst, and the like on the product yield distributions for a number of polymeric materials, each of which is incorporated herein by reference.

In embodiments, the pyrolysis unit can be operated under conditions selected to increase, optimize, or maximize the proportion of the $C_2$-$C_3$ fraction of the pyrolysis gas relative to the $C_4$-$C_5$ fraction of the pyrolysis gas. Conditions for operating the pyrolysis unit may also be selected which can increase, optimize, or maximize proportion of ethylene in the pyrolysis gas versus the other olefins or saturated hydrocarbons. In embodiments, the pyrolysis unit also can be operated under conditions selected to increase, optimize, or maximize the proportion of $C_5$ and lighter ($C_{\leq 5}$) hydrocarbons in the pyrolysis gas relative to $C_6$ and any heavier ($C_{\geq 6}$) hydrocarbons.

In embodiments, the plastic waste can be processed in the pyrolysis unit at a temperature of from about 450° C. to about 800° C. Alternatively, the plastic waste can be processed in the pyrolysis unit at a temperature of from about 600° C. to about 800° C. These temperatures can provide a higher proportion of pyrolysis gas versus pyrolysis oil that conventional operating temperatures provide. In an aspect, the pyrolysis unit can be operated so that the plastic waste is process by pyrolysis at a temperature of about 450° C., about 460° C., about 470° C., about 480° C., about 490° C., about 500° C., about 510° C., about 520° C., about 530° C., about 540° C., about 550° C., about 560° C., about 570° C., about 580° C., about 590° C., about 600° C., about 610° C., about 620° C., about 630° C., about 640° C., about 650° C., about 660° C., about 670° C., about 680° C., about 690° C., about 700° C., about 710° C., about 720° C., about 730° C., about 740° C., about 750° C., about 760° C., about 770° C., about 780° C., about 790° C., or about 800° C., or any ranges between any of these temperatures. It is also contemplated that pyrolysis can be carried out at different temperatures used in different zones of the pyrolysis reactor as will be appreciated by the skilled person. In embodiments, temperature ramps between operating temperatures are contemplated, for example, when adjusting pyrolysis unit operating conditions to increase or decrease the proportion of pyrolysis gas relative to pyrolysis oil.

In another aspect, the plastic waste can be processed in the pyrolysis unit under catalytic conditions in the presence of a catalyst. For example, the plastic waste can be processed in the pyrolysis unit under catalytic conditions using a catalyst comprising alumina, aluminosilicates (for example, zeolites, or silica-alumina), silica-alumina-phosphates, transition metal oxides (for example, titania, zirconia, hafnia, or niobia), polyoxometallates, heteropolyoxometallates, polystyrene sulfonic acid resin, sulfonated carbon, solid phosphoric acid, or niobic acid, or combinations thereof. It is also possible that the plastic waste can be processed in the pyrolysis unit under non-catalytic conditions in the absence of a catalyst.

In an aspect, the pyrolysis unit can be operated continuously, in the same manner as the steam cracker and separation unit and other operations, so that the pyrolysis gas can be supplied continuously. For example, when the pyrolysis furnace temperature is ramped between different operating temperatures to increase or decrease the proportion of pyrolysis gas relative to pyrolysis oil, the unit can continue to supply pyrolysis gas and pyrolysis oil throughout any temperature ramp. In an aspect the pyrolysis gas or a portion thereof can be supplied continuously downstream of the steam cracker according to Aspect I and Aspect II. In another aspect, the pyrolysis unit can be operated intermittently, for example, when adjusting pyrolysis unit operating conditions by changing the catalyst.

In another aspect, the pyrolysis gas may be generated by pyrolyzing plastic waste under conditions which provide pyrolysis gas comprising from about 15 wt. % to about 40 wt. % of ethylene. Alternatively, the pyrolysis gas can comprise from about 18 wt. % to about 38 wt. % of ethylene or from about 20 wt. % to about 35 wt. % of ethylene. In this aspect, the pyrolysis unit can be operated under conditions which provide pyrolysis gas comprising ethylene in a concentration of about 15 wt. %, about 18 wt. %, about 20 wt. %, about 23 wt. %, about 25 wt. %, about 28 wt. %, about 30 wt. %, about 33 wt. %, about 35 wt. %, about 38 wt. %, or about 40 wt. % of ethylene, including any ranges between these values.

According to one aspect, the pyrolysis gas may be generated by pyrolyzing plastic waste under conditions which provide pyrolysis gas comprising from about 25 wt. % to about 60 wt. % of a $C_2$ hydrocarbon (ethane and ethylene). Alternatively the pyrolysis gas can comprise from about 30 wt. % to about 55 wt. % of a $C_2$ hydrocarbon or from about 35 wt. % to about 50 wt. % of a $C_2$ hydrocarbon. In this aspect, the pyrolysis unit can be operated under conditions which provide pyrolysis gas comprising a $C_2$ hydrocarbon in a concentration of about 25 wt. %, about 30 wt. %, about 35 wt. %, about 40 wt. %, about 45 wt. %, about 50 wt. %, about 55 wt. %, or about 60 wt. % of ethylene, including any ranges between these values.

In yet another aspect, the pyrolysis gas may be generated by pyrolyzing plastic waste under conditions which provide pyrolysis gas comprising from about 15 wt. % to about 35 wt. % of propylene. Alternatively the pyrolysis gas can comprise from about 17 wt. % to about 32 wt. % of propylene or from about 20 wt. % to about 30 wt. % of propylene. In this aspect, the pyrolysis unit can be operated under conditions which provide pyrolysis gas comprising propylene in a concentration of about 15 wt. %, about 17 wt. %, about 20 wt. %, about 22 wt. %, about 25 wt. %, about 27 wt. %, about 30 wt. %, about 32 wt. %, or about 35 wt. % of propylene, including any ranges between these values.

In a further aspect of the disclosure, the pyrolysis gas may be generated by pyrolyzing plastic waste under conditions which provide pyrolysis gas comprising from about 17 wt. % to about 45 wt. % of a $C_3$ hydrocarbon (propane and propylene). Alternatively the pyrolysis gas can comprise from about 20 wt. % to about 42 wt. % of a $C_3$ hydrocarbon or from about 22 wt. % to about 40 wt. % of a $C_3$ hydrocarbon. In this aspect, the pyrolysis unit can be operated under conditions which provide pyrolysis gas comprising a $C_3$ hydrocarbon in a concentration of about 17 wt. %, about 20 wt. %, about 22 wt. %, about 25 wt. %, about 27 wt. %, about 30 wt. %, about 32 wt. %, about 35 wt. %, about 37 wt. %, about 40 wt. %, about 42 wt. %, or about 45 wt. % of a $C_3$ hydrocarbon, including any ranges between these values.

In embodiments, the pyrolysis gas may be purified prior to providing the pyrolysis gas to the separation unit as a feed. Regardless of the concentrations of the various components of the pyrolysis gas, any process disclosed herein can further comprise the step of tracking the fuel costs and the total value of the circular products in real time.

The pyrolysis gas and the pyrolysis oil (sometimes abbreviated pygas and pyoil, respectively) of this disclosure can be derived from the pyrolysis of a wide range of plastic wastes. For example, the pyrolysis gas and pyrolysis oil can be derived from pyrolysis of polyolefins of any type such as polyethylene and polypropylene polymers and co-polymers, polystyrene, polyethylene terephthalate (PET), polyvinyl chloride (PVC), polyamides, polycarbonates, polyurethanes, polyesters, copolymers thereof, filled polymers thereof, composites thereof, natural or synthetic rubber, tires, or any combination thereof. For example, the plastic waste can comprise polyethylene, polypropylene, polystyrene, polyethylene terephthalate (PET), polyamide, polycarbonate, polyurethane, or polyester.

In some processes, it may be desirable for the pyrolysis gas and pyrolysis oil to have relatively low concentrations of chloride, which can be accomplished by, for example, selecting plastic wastes having low concentrations of chloride-containing polymers such as PVC. In another aspect, using a pyrolysis gas or pyrolysis oil having relatively low concentrations of chloride may also be accomplished by, for example, purification of the pyrolysis gas or pyrolysis oil prior to using as a feedstock or a co-feedstock.

For example, in an aspect the plastic waste can comprise a chloride-containing polymer, at least a portion of which has been removed from the plastic waste prior to pyrolyzing the plastic waste in the pyrolysis unit. In another aspect, the plastic waste can comprise a chloride-containing polymer, and at least a portion of the chloride-containing pyrolysis products have been removed from the pyrolysis gas or pyrolysis oil prior to feeding to a downstream unit.

In embodiments, the pyrolysis gas or the pyrolysis oil can contain a range of non-hydrocarbon contaminants. For example, the pyrolysis gas or the pyrolysis oil may contain a non-hydrocarbon contaminant that comprises or is selected from an inorganic acid, an organic acid, a binary compound of a group 15 element and hydrogen, a binary compound of a group 16 element and hydrogen, an organic compound comprising a group 15 element, or an organic compound comprising a group 16 element. Examples of non-hydrocarbon contaminant that may occur in the pyrolysis gas or pyrolysis oil include but are not limited to HCl, HBr, phosphine, arsine, stibine, an alcohol, an organic acid, a nitrogen oxide, chloroform, a $C_1$-$C_3$ hydrocarbon chloride, or a $C_1$-$C_3$ hydrocarbon fluoride.

Prior to feeding the pyrolysis gas to the separation unit as in Aspect I, or prior to feeding the pyrolysis gas to the condensing unit as in Aspect II, the pyrolysis gas can pretreated with caustic or an amine, which aids in removal of acidic components. The pyrolysis gas also may be pretreated with a metal oxide, such as in a metal oxide catalyst bed, prior to feeding the pyrolysis gas to the separation unit as in Aspect I or prior to feeding the pyrolysis gas to the condensing unit as in Aspect II. For example, the metal oxide catalyst bed can comprise or can be selected from zinc oxide, calcium oxide, or iron oxide, or various combinations of metal oxides. In some embodiments, the pyrolysis gas can be pretreated with a molecular sieve or a promoted or activated alumina prior to feeding the pyrolysis gas to the separation unit, a condensing unit, or any downstream unit.

Subsequent Processing of Pyrolysis Unit and Separation Unit Effluents. Once the plastic waste has been pyrolyzed and processed as disclosed herein, a range of circular products can be provided, and number of subsequent processing steps can be carried out for producing other circular chemicals or circular polymers and for recycling certain effluents. For example, in accordance with the processes of Aspect I and Aspect II described above, ethylene, propylene, and light ($C_2$-$C_3$) saturated hydrocarbons can be formed and separated and used in downstream processes.

For example, the processes disclosed herein can further comprise the step of feeding the ethylene effluent or at least a portion of the ethylene effluent to one or more downstream processing units to provide a circular product comprising or selected from ethylene homopolymers, ethylene-alpha-olefin copolymers, ethylene-ionomer copolymers, ethylene-propylene elastomers, normal alpha-olefins ($C_4$-$C_{30}$+), chlorosulfonated polyethylene, vinyl chloride, ethylene oxide, ethylbenzene, acetaldehyde, vinyl acetate, or polyvinyl acetate. The circular ethylene effluent or a portion thereof can be provided as a feed to a polymerization reactor and converted to any type of circular polyethylene or other circular products derived from ethylene, for example, ethylbenzene. Each of these circular products can be subsequently processed to provide further circular chemicals and polymers, some examples of which are described hereinbelow.

In one aspect, for example, when one or more downstream processing units provides circular vinyl chloride, the circular vinyl chloride can be fed to one or more subsequent processing units to provide a circular product selected from polyvinyl chloride homopolymers, polyvinyl chloride copolymers, vinyl chloride-vinyl acetate copolymers, 1,1,2-trichloroethane, vinylidene chloride, or polyvinylidene chloride.

When the one or more downstream processing unit provides circular ethylene oxide, in a further aspect the circular ethylene oxide can be fed to one or more subsequent processing units to provide a circular product selected from ethylene glycol, poly(ethylene terephthalate), polyethylene glycol-polyalkylene glycol copolymers, ethoxylated phenols, ethoxylated amines, diethylene glycol, polyester, unsaturated polyester, polyester polyols, adipic acid, polyurethane resins, hydroxyethyl starch, hydroxyethyl gums, or hydroxyethyl cellulose.

In still a further aspect, when the one or more downstream processing unit provides circular ethylbenzene, the circular ethylbenzene can be fed to one or more subsequent processing units to provide a circular product selected from styrene, polystyrene, styrene-butadiene copolymers, acrylonitrile-butadiene-styrene terpolymers, styrene-acrylonitrile copolymers, polyester resins, styrene-divinylbenzene resin, styrene-alkyd copolymers, or styrene-maleic anhydride copolymers.

According to still another aspect, when the one or more downstream processing unit provides circular acetaldehyde, the circular acetaldehyde can be fed to one or more subsequent processing units to provide a circular product selected from pentaerythritol, alkyd resins, or acetic acid.

In the event the one or more downstream processing unit provides circular vinyl acetate, in an aspect the circular vinyl acetate can be fed to one or more subsequent processing units to provide a circular product selected from poly(vinyl acetate), poly(vinyl acetate) copolymers, ethylene-vinyl acetate copolymers, or vinyl chloride-vinyl acetate copolymers.

According to yet another aspect, when the one or more downstream processing unit provides circular poly(vinyl acetate), the circular poly(vinyl acetate) can be fed to one or more subsequent processing units to provide a circular product selected from poly(vinyl alcohol), poly(vinyl butyral), poly(vinyl formal).

In a further aspect, when the one or more downstream processing unit provides circular α-olefin, the circular α-olefin can be fed to one or more subsequent processing units to provide a circular product selected from poly-α-olefin or poly(ethylene-co-α-olefin). For example, the circular α-olefin can be a circular normal-α-olefins ($C_4$-$C_{30}$+), and the circular normal-α-olefins ($C_4$-$C_{30}$+) can be fed to one or more subsequent processing units to provide a circular product selected from poly-(normal-α-olefin) or poly(ethylene-co-(normal-α-olefin)).

In another aspect, the one or more downstream processing unit can provide circular α-olefin which comprises or is selected from 1-butene, 1-pentene, 1-hexene, 1-heptene, 1-octene, 1-nonene, 1-decene, 1-dodecene, 1-tetradecene, 1-hexadecene, or 1-octadecene, and these circular α-olefins can be fed to one or more subsequent processing units to provide a circular product comprising or selected from from poly(ethylene-co-1-butene), poly(ethylene-co-1-pentene), poly(ethylene-co-1-hexene), poly(ethylene-co-1-heptene), poly(ethylene-co-1-octene), poly(ethylene-co-1-nonene), poly(ethylene-co-1-decene), poly(ethylene-co-1-dodecene), poly(ethylene-co-1-tetradecene), poly(ethylene-co-1-hexadecene), or poly(ethylene-co-1-octadecene).

The plastic waste which has been pyrolyzed can also provide a circular propylene effluent as disclosed above, and any number of subsequent processing steps also may be carried out for producing other circular chemicals or circular polymers from circular propylene. In one aspect, for example, the processes disclosed herein can further comprise the step of feeding the propylene effluent or at least a portion of the propylene effluent to one or more downstream processing units to provide a circular product comprising or selected from polypropylene homopolymers, polypropylene copolymers, acrylonitrile, propylene oxide, cumene, n-butyraldehyde, isobutyraldehyde, allyl chloride, acrylic acid esters, or isopropyl alcohol. For example, the propylene effluent or at least a portion thereof can be provided as a feed to a polymerization reactor to form a circular polypropylene.

In another aspect, when the one or more downstream processing units provides circular acrylonitrile, the circular acrylonitrile can be fed to one or more subsequent processing units to provide a circular product selected from polyacrylonitrile, modacrylic copolymers, acrylonitrile butadiene styrene (ABS), styrene acrylonitrile resin (SAN), nitrile elastomers, acrylonitrile copolymers, hexamethylene diamine, nylon 6,6, acrylamide, polyacrylamide homopolymers, or polyacrylamide copolymers.

According to one aspect, when the one or more downstream processing units provides circular propylene oxide, the circular propylene oxide can be fed to one or more subsequent processing units to provide a circular product selected from propylene glycol, polyesters, poly(propylene glycols) homopolymers, poly(propylene glycols) copolymers, or polyurethanes.

In a further aspect, when the one or more downstream processing units provides circular n-butyraldehyde, the circular n-butyraldehyde can be fed to one or more subsequent processing units to provide a circular product selected from poly(vinyl butyral), n-butyric acid, n-butyric anhydride, or cellulose acetate butyrate.

In still another aspect, when the one or more downstream processing units provides circular isobutyraldehyde, the circular isobutyraldehyde may be fed to one or more subsequent processing units to provide a circular product selected from neopentyl glycol, polyesters, or polyurethanes.

According to a further aspect, when the one or more downstream processing units provides circular allyl chloride, the circular allyl chloride can be fed to one or more subsequent processing units to provide a circular product selected from epichlorohydrin or epoxy resins.

In yet another aspect, when the one or more downstream processing units provides circular acrylic acid esters, the circular acrylic acid esters can be fed to one or more subsequent processing units to provide a circular product selected from acrylic homopolymers or copolymers.

In still a further aspect, when the one or more downstream processing units provides circular isopropyl alcohol, the circular isopropyl alcohol can be fed to one or more subsequent processing units to provide a circular product selected from acetone, bisphenol A, epoxy resins, polycarbonates, polysulfones, methacrylic acid, poly(methyl methacrylate) homopolymers or poly(methyl methacrylate) copolymers.

In some embodiments, plastic waste which has been pyrolyzed can be processed as described to provide a variety of circular products such as ethylene, propylene, light ($C_2$-$C_3$) saturated hydrocarbons, and other products. For example, in accordance with the processes of Aspect I and Aspect II described above, ethylene, propylene, and light ($C_2$-$C_3$) saturated hydrocarbons can be formed and separated. However, additional products also may be produced in these processes and separated downstream. In both Aspect I and Aspect II, the $C_5$ and lighter hydrocarbon pyrolysis gases or a fraction thereof can be fed downstream of a steam cracking furnace, mixed with the effluent from a steam cracking furnace, then purified or separated, and subsequently fed to other subsequent processes or reactors. In these processes, the separation steps can provide circular products which further comprise a butenes and butane effluent. The butenes and butane effluent can be used in any number of downstream processes for producing other circular chemicals or circular polymers.

In an aspect, for example, the butenes and butane effluent or a portion thereof can be fed to one or more downstream processing units to provide a circular product comprising or selected from circular butadiene, maleic anhydride, butylene oxide, 1-butene, mixed butenes, isobutene, or butane.

In an aspect, when the one or more downstream processing units provides circular butadiene, the circular butadiene can be used as a feed to one or more subsequent processing units to provide a circular product selected from circular styrene, polybutadiene elastomer, polybutadiene resins, hexamethylene diamine, nylons, chloroprene, neoprene elastomer, 1,5-cyclooctadiene, ethylene-propylene terpolymer elastomer, 1,5,9-cyclododecatriene, dodecanoic acid, nylon 6,12, qiana, lauryl lactam, nylon 12, OH-terminated polymers and copolymers, polyurethane elastomers, or 1,4-hexadiene.

Another aspect provides that when the one or more downstream processing units provides circular maleic anhydride, the circular maleic anhydride can be fed to one or more subsequent processing units to provide a circular product selected from circular polyesters, alkyd resins, or styrene-maleic anhydride copolymer.

Still another aspect provides that when the one or more downstream processing units provides circular butylene oxide, the circular butylene oxide can be fed to one or more subsequent processing units to provide a circular product selected from circular poly(butylene oxide) or polyurethanes.

When the one or more downstream processing units provides circular 1-butene, mixed butenes, and/or isobutene, in an aspect the circular 1-butene, mixed butenes, and/or isobutene can be fed to one or more subsequent processing units to provide a circular product selected from circular poly(1-butene), poly(butene), poly(isobutene), or butyl rubber.

In a further aspect, when the one or more downstream processing units provides circular butane, the circular butane can be fed to one or more subsequent processing units to provide a circular product selected from circular acetic acid.

For these circular products, as with any circular product described herein, the weight or fraction of the circular product which is attributable to the pyrolysis gas or plastic waste can be determined by mass balance. In a further aspect, any one or more of these circular products may be certified in accordance with International Sustainability and Carbon Certification (ISCC) standards, based upon the weight or fraction of the circular product attributable to the pyrolysis gas or the plastic waste, as determined by mass balance and the free attribution method.

When the ethylene effluent produced according to this disclosure, for example according to Aspect I or Aspect II, is fed to a polymerization reactor to form a circular polyethylene, the amount of circular polyethylene produced can be from about 10%, about 15%, about 20%, or about 25% greater, or any range therebetween, than the amount of circular polyethylene produced in a corresponding process that uses a liquid pyrolysis effluent feedstock only, as quantified by a percent (%) of gas yield from the pyrolysis unit per unit weight of plastic feed.

In a further aspect, the carbon footprint of any independently selected circular product can be reduced by about 15%, about 20%, about 25%, about 30%, about 35%, or about 40% as compared to a carbon footprint a corresponding non-circular product produced in the absence of the pyrolysis gas and the pyrolysis oil.

According to another aspect, the plastic waste can be pyrolyzed in an amount sufficient to displace about 1 wt. %, about 2 wt. %, about 3 wt. %, about 4 wt. %, about 5 wt. %, about 6 wt. %, about 7 wt. %, about 8 wt. %, about 9 wt. %, or about 10 wt % of a virgin feedstock required to produce the same amount of the ethylene effluent, the propylene effluent, and the light ($C_2$-$C_3$) saturated hydrocarbon effluent from a separation unit downstream of a steam cracker furnace.

A further aspect provides that the plastic waste can be pyrolyzed in an amount sufficient to provide about 1 wt. %, about 2 wt. %, about 3 wt. %, about 4 wt. %, about 5 wt. %, about 6 wt. %, about 7 wt. %, about 8 wt. %, about 9 wt. %, or about 10 wt % of the separation unit feed.

Pyrolysis of Plastic Waste to Produce Light Gaseous Hydrocarbons and Integration of a Pyrolysis Unit with a Fluid Catalytic Cracker. Regarding Aspect VI of this disclosure, there is provided a process for recycling plastic waste which includes producing chemicals or polymers from plastic waste, the process comprising:

(a) pyrolyzing a plastic waste in a pyrolysis unit to produce a pyrolysis unit effluent comprising a pyrolysis gas and a pyrolysis oil, wherein the pyrolysis gas comprises $C_5$ and lighter ($C_{\leq 5}$) hydrocarbons having a $C_2$-$C_3$ fraction and a $C_4$-$C_5$ fraction;
(b) feeding a heavy hydrocarbon feed stream to a fluid catalytic cracker (FCC) reactor to produce an FCC effluent comprising naphtha ($C_6$-$C_{10}$ hydrocarbons) and $C_5$ and lighter ($C_{\leq 5}$) hydrocarbons;
(c) providing a fractionation unit feed comprising at least a portion of the pyrolysis gas and at least a portion of the FCC effluent to a fractionation unit; and
(d) separating the fractionation unit feed to provide circular products comprising a first fractionation effluent comprising $C_5$ and lighter ($C_{\leq 5}$) hydrocarbons and a second fractionation effluent comprising heavy ($C_{6+}$) hydrocarbons.

In this aspect, the $C_5$ and lighter hydrocarbon gas stream, with or without the condensable components, may be fed downstream of an FCC to the reactor effluent purification/separation unit. The pyrolysis gas either can be fed directly to the fractionation unit, or the FCC effluent and the pyrolysis gas can be combined to form the fractionation unit feed prior being fed to the fractionation unit.

Regarding the FCC reactor, in an aspect the heavy hydrocarbon feed stream can be fed to a fluid catalytic cracker (FCC) pretreater to form a treated stream, prior to feeding the treated stream to the FCC reactor. For example, the treated stream may have a lower sulfur content, a lower aromatic content, or both, as compared with the sulfur content and/or aromatic content in the heavy hydrocarbon feed stream prior to pretreating.

Regarding the fractionation unit feed, in this aspect, the fractionation unit feed can further include at least a portion of the pyrolysis oil in the pyrolysis unit effluent produced from pyrolyzing plastic waste.

In an aspect, at least a portion of the second fractionation effluent comprising heavy ($C_{6+}$) hydrocarbons can be recycling to the fluid catalytic cracker (FCC) reactor if desired.

When the fractionation unit feed is separated to provide circular products which include a first fractionation effluent comprising $C_5$ and lighter hydrocarbons and a second fractionation effluent comprising heavy hydrocarbons, the second fractionation effluent comprising heavy ($C_{6+}$) hydrocarbons or a portion thereof may be fed to a reforming unit or an AROMAX® unit to provide a reforming product stream or an AROMAX® product stream, respectively, each comprising circular aromatic hydrocarbons. In an aspect, the reforming product stream or the AROMAX® product stream may further comprise hydrogen and/or aliphatic hydrocarbons.

The circular aromatic hydrocarbon products provided in the reforming product stream or the AROMAX® product stream may be fed to one or more subsequent processing units to provide a number of circular products, examples of which include the following.

In aspects, the reforming product stream or the AROMAX® product stream can include circular benzene, and the circular benzene is fed to one or more subsequent processing units to provide a circular product selected from ethylbenzene, benzenesulfonic acid, chlorobenzene, cumene, cyclohexane, nitrobenzene, or maleic anhydride. The reforming product stream or the AROMAX® product stream can include circular toluene, and the circular toluene may be fed to one or more subsequent processing units to provide a circular product selected from dinitrotoluenes, toluene diisocyanate, or urethanes.

In other aspects, the reforming product stream or the AROMAX® product stream can include circular o-xylene, and the circular o-xylene can be fed to one or more subsequent processing units to provide a circular product selected from phthalic anhydride, alkyd resins, polyester resins, polyester polyols, urethanes, or polyurethanes. The reforming product stream or the AROMAX® product stream also can include circular m-xylene, which may be fed to one or more subsequent processing units to provide a circular product selected from isophthalic acid, polyesters, alkyd resins, polyamide resins, diphenyl isophthalate, or polybenzimidazoles. The reforming product stream or the AROMAX® product stream also may include circular p-xylene, and the circular p-xylene can be fed to one or more subsequent processing units to provide a circular product selected from terephthalic acid, poly(ethylene terephthalate), or poly(butylene terephthalate).

In each of the processes, the fraction of aromatic hydrocarbons in the reforming product stream or the AROMAX® product stream attributable to the plastic waste or pyrolysis gas can be determined by mass balance. The fraction of benzene, toluene, o-xylene, m-xylene, p-xylene, or any circular product produced in the one or more subsequent processing units attributable to the plastic waste or pyrolysis gas also be determined by mass balance. The benzene, toluene, o-xylene, m-xylene, p-xylene, or any circular product produced in the one or more subsequent processing units attributable to the plastic waste or pyrolysis gas also may be certified as circular in accordance with International Sustainability and Carbon Certification (ISCC) standards, based upon the weight or fraction of the circular product attributable to the plastic waste, as determined by mass balance and the free attribution method.

Further related to Aspect VI set out above and aspects related thereto, these processes may further comprise the step of feeding at least a portion of the first fractionation effluent comprising $C_5$ and lighter ($C_{\leq 5}$) hydrocarbons to a steam cracking furnace to form a steam cracker product stream comprising ethylene and light ($C_2$-$C_3$) saturated hydrocarbons. The steam cracker product stream may then be fed to a separation unit, and this separation unit feed may be separated to provide an ethylene effluent, a propylene effluent, and a light ($C_2$-$C_3$) saturated hydrocarbon effluent. If desired, the light ($C_2$-$C_3$) saturated hydrocarbon effluent or a portion thereof can be recycled to the steam cracking furnace. The ethylene effluent, the propylene effluent, or portions thereof may be fed to a polymerization reactor to form a circular polyethylene or a circular polypropylene. In any of these processes, the fraction of the product such as circular polyethylene or circular polypropylene which is attributable to the plastic waste or the pyrolysis gas is determined by mass balance, and these products may be certified as circular in accordance with International Sustainability and Carbon Certification (ISCC) standards, based upon the weight or fraction of the circular product attributable to the plastic waste, as determined by mass balance and the free attribution method.

The present disclosure is further illustrated by the following examples, which are not to be construed in any way as imposing limitations upon the scope thereof. On the contrary, it is to be clearly understood that resort can be had to various other aspects, embodiments, modifications, and equivalents thereof which, after reading the description herein, may suggest themselves to one of ordinary skill in the art without departing from the spirit of the present invention or the scope of the appended claims.

EXAMPLES

General Considerations

Certification calculations of percent circular product. The ISCC Sustainability Declarations are issued for discrete mass quantities of product, therefore certification is for a particular product weight. Conversion factors for use in the certification calculation may vary considerably depending upon the particular reactor, processing unit, and conditions, and conversion factors are predetermined and therefore backward looking. Conversion factors can be re-determined as required for certification, for example in the absence of a change in processing conditions, conversion factors can be re-determined and adjusted annually. The certification calculation of the weight of circular product is based upon the assumption that most of the weight of the pyrolysis oil added into the cracker and mixed with the petroleum-based or fossil fuel-based feed is also manifested in the circular product. Therefore, this calculation assumes that the conversion rate applies to the pyrolysis oil portion of the feed as well as the petroleum-based feedstock or fossil fuel-based feedstock.

Therefore, this certification process uses a free attribution method to assign circular product credit to every product stream, minus any waste streams such as the portion of the stream which is flared. Moreover, the free attribution method allows all the credit produced from mixing a pyrolysis oil stream with a petroleum-based or fossil fuel-based feed to be distributed as desired to any or all of the processing unit (e.g. cracker) products from that stream, again less any waste stream. For example, as long as pyrolysis oil is used to generate ethylene, propylene, fuel gas, and any other product which is recovered from a stream, the total circular product credit from all the recovered product can be taken as circular ethylene.

This free attribution method is reasonably grounded in the measured or calculated conversion factors for the various plants or units which are reflected in this disclosure, which may have conversion factors of >0.90, for example, in a range of from about 0.90 to about 0.998. Therefore, to determine the weight of circular ethylene produced, this ca. 1 conversion factor is multiplied by the weight of pyrolysis oil fed to the cracker. This free attribution principle is also applied to the polyethylene (PE) reactor and the fluid catalytic cracker (FCC), which have similarly high conversion factors. The application of this calculation method is demonstrated in the examples below.

Example 1. Certification Calculation for the Production of Ethylene

A feed containing 10 wt % concentration of pyrolysis oil mixed with petroleum-based or fossil fuel-based feedstock is fed to a cracker. It has been previously calculated over a discrete time period that the cracker converts the feedstock into ethylene (60 wt %), propylene (25 wt %), and fuel gas (12 wt %) mix accounting for 97 wt % recovered product, with the remaining 3 wt % flared. Therefore in this example, the calculated conversion factor for the cracker is 0.97 for the previous time period. Every hundred pounds of total feedstock contain 10 pounds of pyrolysis oil (10 wt % concentration), with the balance being the petroleum-based or fossil fuel-based feed. The weight of circular product attributed to the pyrolysis oil can therefore be calculated as 9.7 pounds (10 pounds×0.97 conversion factor). The entire amount of the 9.7 pounds of circular product is attributed to the recovered ethylene for circularity. Therefore, the resulting circular ethylene is certified as 9.7 pounds in accordance with the ISCC standards.

Example 2. Certification Calculation for the Production of Ethylene Homopolymer

The ethylene produced according to Example 2 containing circular product is fed to a polymerization reactor and converted to ethylene homopolymer. Therefore, 60 pounds of ethylene (100 pounds feedstock×60 wt %) are calculated to contain 9.7 pounds of circular ethylene. It has been previously calculated over a discrete time period that the polymerization reactor converts an ethylene feedstock into polyethylene (98 wt %), with the remaining 2 wt % discarded, therefore in this example, the calculated conversion factor for the polymerization reactor is 0.98 for the previous time period.

The total polyethylene product from 60 pounds of ethylene is 58.8 pounds (60 pounds total ethylene×0.98 conversion factor). The weight of circular polyethylene product attributed to the pyrolysis oil can therefore be calculated as 9.5 pounds (9.7 pounds circular ethylene×0.98 conversion factor) and certified as 9.5 pounds in accordance with the ISCC standards.

Example 3. Certification Calculation for the Production of Ethylene Copolymer

The ethylene produced according to Example 2 containing circular product is fed to a polymerization reactor with non-circular comonomer 1-hexene and converted to poly (ethylene-co-1-hexene) copolymer. Therefore, 60 pounds of ethylene (100 pounds feedstock×60 wt %) are calculated to contain 9.7 pounds of circular ethylene. It has been previously calculated over a discrete time period that the polymerization reactor converts an ethylene and 1-hexene feed into poly(ethylene-co-1-hexene) (98 wt %), with the remaining 2 wt % discarded, therefore in this example also, the calculated conversion factor for the polymerization reactor is 0.98 for the previous time period.

The total poly(ethylene-co-1-hexene) product from 60 pounds of ethylene is therefore 58.8 pounds (60 pounds total ethylene×0.98 conversion factor). The weight of circular poly(ethylene-co-1-hexene) product attributed to the pyrolysis oil can therefore be calculated as 9.5 pounds (9.7 pounds circular poly(ethylene-co-1-hexene)×0.98 conversion factor) and certified as 9.5 pounds in accordance with the ISCC standards.

Example 4. Certification Calculation for the Production of Ethylene Copolymer

The ethylene produced according to Example 2 containing circular product is fed to a polymerization reactor with circular comonomer 1-hexene and converted to poly(ethylene-co-1-hexene) copolymer. Therefore, 60 pounds of ethylene (100 pounds feedstock×60 wt %) are calculated to contain 9.7 pounds of circular ethylene. The feed in this example can contain 60 pounds of ethylene (9.7 pounds circular) and 5 pounds 1-hexene, of which 1 pounds is certified as circular, for a total feed of 65 pounds with 10.7 pounds (9.7 pounds circular ethylene+1 pounds circular 1-hexene) of the feed being certified as circular. It has been previously calculated over a discrete time period that the polymerization reactor converts an ethylene and 1-hexene feed into poly(ethylene-co-1-hexene) (98 wt %), with the remaining 2 wt % discarded, therefore in this example also, the calculated conversion factor for the polymerization reactor is 0.98 for the previous time period.

The total poly(ethylene-co-1-hexene) product from this 65 pounds of feed is therefore 63.7 pounds (65 pounds total feed×0.98 conversion factor). The weight of circular poly (ethylene-co-1-hexene) product attributed to the pyrolysis oil can therefore be calculated as 10.49 pounds [(9.7 pounds circular ethylene×0.98 conversion factor)+(1 pounds circular 1-hexene×0.98 conversion factor)] and certified as 10.49 pounds in accordance with the ISCC standards. This circular product of 10.49 pounds can also be readily calculated using the 10.7 pounds of circular product in the 65 pounds of feed×0.98 conversion factor.

Example 5. Certification Calculation for the Production of Ethylbenzene

The principles illustrated above can be applied to other products and the certification of a certain weight of product produced as circular in accordance with the ISCC standards can be calculated. In this example, a benzene comprising circular benzene is reacted with ethylene comprising circular ethylene in a catalyzed reaction to produce ethylbenzene. Each hundred pounds of total feedstock contain 10 pounds of circular benzene and 5 pounds of circular ethylene. It has been previously calculated over a discrete time period that this reactor converts a benzene and ethylene feed into a mix of ethylbenzene (95 wt %) plus 3% other products which are recovered, with the remaining 2 wt % discarded. Therefore in this example, the calculated conversion factor for the reaction unit is 0.98 for the previous time period.

The total ethylbenzene product from 100 pounds of total feed is therefore 95 pounds (100 pounds total feed×95 wt %). The weight of circular ethylbenzene attributed to the circular benzene and circular ethylene can therefore be calculated as 14.7 pounds [(10 pounds circular benzene× 0.98 conversion factor)+(5 pounds circular ethylene×0.98 conversion factor)] and certified as 14.7 pounds in accordance with the ISCC standards.

These and other features or embodiments of the disclosure can further include the various aspects that are presented in the Aspects of the Disclosure set out below.

ASPECTS OF THE DISCLOSURE

Aspect 1. A process for recycling plastic waste, the process comprising:
(a) pyrolyzing a plastic waste in a pyrolysis unit under a first set of pyrolysis conditions to produce a pyrolysis unit effluent comprising a pyrolysis gas and a pyrolysis oil in a known ratio and separating the pyrolysis gas from the pyrolysis oil, wherein the pyrolysis gas comprises $C_5$ and lighter ($C_1$, $C_2$, $C_3$, $C_4$, and $C_5$) hydrocarbons, including ethylene, propylene, and butylene (EPB);
(b) feeding a first feed stream to a steam cracker furnace to produce a steam cracker furnace effluent comprising ethylene, propylene, and light ($C_2$-$C_3$) saturated hydrocarbons;
(c) providing to a separation unit a separation unit feed comprising at least a portion of the pyrolysis gas and at least a portion of the steam cracker furnace effluent; and
(d) separating the separation unit feed to provide circular products comprising an ethylene effluent, a propylene effluent, and a light ($C_2$-$C_3$) saturated hydrocarbon effluent.

Aspect 2. The process for recycling plastic waste according to any of the preceding Aspects, wherein the pyrolysis gas and the steam cracker furnace effluent are combined to form the separation unit feed.

Aspect 3. The process for recycling plastic waste according to any of the preceding Aspects, further comprising the step of:
compressing the pyrolysis gas prior to providing at least a portion of the pyrolysis gas as a separation unit feed to the separation unit.

Aspect 4. A process for recycling plastic waste, the process comprising:
(a) pyrolyzing a plastic waste in a pyrolysis unit under a first set of pyrolysis conditions to produce a pyrolysis unit effluent comprising a pyrolysis gas and a pyrolysis oil in a known ratio and separating the pyrolysis gas from the pyrolysis oil, wherein the pyrolysis gas comprises $C_5$ and lighter ($C_1$, $C_2$, $C_3$, $C_4$, and $C_5$) hydrocarbons, including ethylene, propylene, and butylene (EPB);
(b) providing the pyrolysis gas to a condensing unit and forming a first condenser effluent having a higher proportion of $C_4$-$C_5$ hydrocarbons than the pyrolysis gas and a second condenser effluent having a higher proportion of $C_2$-$C_3$ hydrocarbons than the pyrolysis gas;
(c) feeding a first feed stream to a steam cracker furnace to produce a steam cracker furnace effluent comprising ethylene, propylene, and light ($C_2$-$C_3$) saturated hydrocarbons;
(d) providing to a separation unit a separation unit feed comprising at least a portion of the second condenser effluent and at least a portion of the steam cracker furnace effluent; and
(e) separating the separation unit feed to provide circular products comprising an ethylene effluent, a propylene effluent, and a light ($C_2$-$C_3$) saturated hydrocarbon effluent.

Aspect 5. The process for recycling plastic waste according to Aspect 4 wherein:
the second condenser effluent and the steam cracker furnace effluent are combined prior to step (d) to form the separation unit feed.

Aspect 6. The process for recycling plastic waste according to any of Aspects 4-5, further comprising the step of:
feeding at least a portion of the first condenser effluent to the steam cracker furnace.

Aspect 7. The process for recycling plastic waste according to any of Aspects 4-6, wherein:
the first condenser effluent and the first feed stream are combined prior to feeding to the steam cracking furnace.

Aspect 8. A process for recycling plastic waste according to any of the preceding Aspects, the process further comprising the steps of:
(a') assigning a market price to the pyrolysis oil formed under the first set of pyrolysis conditions as equivalent to a market price of a reference liquid product;
(b') determining a market price of the combined ethylene, propylene, and butylene (EPB) in the pyrolysis gas formed under the first set of pyrolysis conditions; and
(c') (1) when the market price of the combined EPB is greater than the market price of the pyrolysis oil, applying a second set of pyrolysis conditions which increase the proportion of pyrolysis gas relative to the pyrolysis oil in the pyrolysis reactor effluent; or (2) when the market price of the pyrolysis oil is greater than the market price of the combined EPB formed under the first set of conditions, applying a second set of pyrolysis conditions which increase the proportion of pyrolysis oil relative to the pyrolysis gas in the pyrolysis reactor effluent.

Aspect 9. A process for recycling plastic waste, the process comprising:

(a) pyrolyzing a plastic waste in a pyrolysis unit under a first set of pyrolysis conditions to produce a pyrolysis unit effluent comprising a pyrolysis gas and a pyrolysis oil in a known ratio and separating the pyrolysis gas from the pyrolysis oil, wherein the pyrolysis gas comprises $C_5$ and lighter ($C_1$, $C_2$, $C_3$, $C_4$, and $C_5$) hydrocarbons, including ethylene, propylene, and butylene (EPB);

(b) assigning a market price to the pyrolysis oil formed under the first set of pyrolysis conditions as equivalent to a market price of a reference liquid product;

(c) determining a market price of the combined ethylene, propylene, and butylene (EPB) in the pyrolysis gas formed under the first set of pyrolysis conditions; and (d) (1) when the market price of the combined EPB is greater than the market price of the pyrolysis oil, applying a second set of pyrolysis conditions which increase the proportion of pyrolysis gas relative to the pyrolysis oil in the pyrolysis reactor effluent; or (2) when the market price of the pyrolysis oil is greater than the market price of the combined EPB formed under the first set of conditions, applying a second set of pyrolysis conditions which increase the proportion of pyrolysis oil relative to the pyrolysis gas in the pyrolysis reactor effluent.

Aspect 10. A process for recycling plastic waste, the process comprising:

(a) pyrolyzing a plastic waste in a pyrolysis unit under a first set of pyrolysis conditions to produce a pyrolysis unit effluent comprising a pyrolysis gas and a pyrolysis oil in a known ratio and separating the pyrolysis gas from the pyrolysis oil, wherein the pyrolysis gas comprises $C_5$ and lighter ($C_1$, $C_2$, $C_3$, $C_4$, and $C_5$) hydrocarbons, including ethylene, propylene, and butylene (EPB);

(b) feeding a first feed stream to a steam cracker furnace to produce a steam cracker furnace effluent comprising ethylene, propylene, and light ($C_2$-$C_3$) saturated hydrocarbons;

(c) providing to a separation unit a separation unit feed comprising at least a portion of the pyrolysis gas and at least a portion of the steam cracker furnace effluent;

(d) assigning a market price to the pyrolysis oil formed under the first set of pyrolysis conditions as equivalent to a market price of a reference liquid product;

(e) determining a market price of the combined ethylene, propylene, and butylene (EPB) in the pyrolysis gas formed under the first set of pyrolysis conditions; and (f) (1) when the market price of the combined EPB is greater than the market price of the pyrolysis oil, applying a second set of pyrolysis conditions which increase the proportion of pyrolysis gas relative to the pyrolysis oil in the pyrolysis reactor effluent; or (2) when the market price of the pyrolysis oil is greater than the market price of the combined EPB formed under the first set of conditions, applying a second set of pyrolysis conditions which increase the proportion of pyrolysis oil relative to the pyrolysis gas in the pyrolysis reactor effluent.

Aspect 11. The process for recycling plastic waste according to any of Aspects 8-10, wherein assigning a market price to the pyrolysis oil comprises assigning a market price to each distillation cut in the pyrolysis oil as equal to a market price of an equivalent reference liquid product for each distillation cut.

Aspect 12. The process for recycling plastic waste according to Aspect 11, wherein the market price to the pyrolysis oil comprises a weighted average of the equivalent reference liquid product for each distillation cut.

Aspect 13. The process for recycling plastic waste according to any of Aspects 11-12, wherein the distillation cuts of the pyrolysis oil comprise any combination of distillation cuts selected from diesel, gasoline, naphtha, kerosene, gas oil, and waxes.

Aspect 14. The process for recycling plastic waste according to any of Aspects 8-13, further comprising the step of tracking the market price of the combined EPB and the market price of the reference liquid product in real time.

Aspect 15. The process for recycling plastic waste according to any of Aspects 8-14, wherein the reference liquid product comprises gasoline, diesel, or a blend of gasoline and diesel.

Aspect 16. The process for recycling plastic waste according to any of Aspects 8-14, wherein the reference liquid product comprises a blend of gasoline and diesel having about 95 wt % to 5 wt % gasoline and about 5 wt % to 95 wt % diesel.

Aspect 17. The process for recycling plastic waste according to any of Aspects 8-14, wherein the reference liquid product comprises a blend of gasoline and diesel having about 90 wt % to 50 wt % gasoline and about 10 wt % to 50 wt % diesel.

Aspect 18. The process for recycling plastic waste according to any of Aspects 8-14, wherein the reference liquid product comprises a blend of gasoline and diesel having about 70 wt % gasoline and about 30 wt % diesel.

Aspect 19. The process for recycling plastic waste according to any of Aspects 8-18, wherein applying the second set of pyrolysis conditions increases the proportion of pyrolysis gas relative to the pyrolysis oil in the pyrolysis reactor effluent.

Aspect 20. The process for recycling plastic waste according to any of Aspects 8-19, wherein applying the second set of pyrolysis conditions provides a pyrolysis reactor effluent having from about 60 wt % to about 85 wt % pyrolysis gas, and having from about 40 wt % to about 15 wt % pyrolysis liquid.

Aspect 21. The process for recycling plastic waste according to any of Aspects 8-19, wherein applying the second set of pyrolysis conditions provides a pyrolysis reactor effluent having from about 75 wt % to about 83 wt % pyrolysis gas, and having from about 25 wt % to about 17 wt % pyrolysis liquid.

Aspect 22. The process for recycling plastic waste according to any of Aspects 8-21, wherein applying the second set of pyrolysis conditions increases the proportion of pyrolysis gas relative to the pyrolysis oil in the pyrolysis reactor effluent, and wherein the pyrolysis oil produced under the second set of pyrolysis conditions has a higher aromatic content than that of the pyrolysis oil produced under the second set of pyrolysis conditions.

Aspect 23. The process for recycling plastic waste according to any of Aspects 8-22, wherein applying the second set of pyrolysis conditions increases the proportion of pyrolysis gas relative to the pyrolysis oil in the pyrolysis reactor effluent, and wherein the pyrolysis oil produced under the second set of pyrolysis conditions has a lower wax content than that of the pyrolysis oil produced under the second set of pyrolysis conditions.

Aspect 24. The process for recycling plastic waste according to any of Aspects 8-18, wherein applying the second set of pyrolysis conditions increases the proportion of pyrolysis oil relative to the pyrolysis gas in the pyrolysis reactor effluent, Aspect 25. The process for recycling plastic waste according to any of Aspects 8-24, further comprising the step of:

certifying the pyrolysis oil, the pyrolysis gas, or any subsequent product produced using the pyrolysis oil or the pyrolysis gas as circular in accordance with International Sustainability and Carbon Certification (ISCC) standards, based upon the weight or fraction of the circular product attributable to the plastic waste, as determined by mass balance and the free attribution method.

Aspect 26. The process for recycling plastic waste according to any of the preceding Aspects, wherein the weight or fraction of the circular products which is attributable to the pyrolysis gas or plastic waste is determined by mass balance.

Aspect 27. The process for recycling plastic waste according to any of the preceding Aspects, further comprising the step of:

certifying any one or more of the circular products from the separation unit as a circular product in accordance with International Sustainability and Carbon Certification (ISCC) standards, based upon the weight or fraction of the circular product attributable to the pyrolysis gas or the plastic waste, as determined by mass balance and the free attribution method.

Aspect 28. The process for recycling plastic waste according to any of the preceding Aspects, further comprising the step of:

recycling at least a portion of the light ($C_2$-$C_3$) saturated hydrocarbon effluent to the steam cracking furnace.

Aspect 29. The process for recycling plastic waste according to Aspect 28, wherein the light ($C_2$-$C_3$) saturated hydrocarbon effluent is treated to remove contaminants prior to recycling at least a portion of the light saturated hydrocarbon effluent to the steam cracking furnace.

Aspect 30. The process for recycling plastic waste according to any of the preceding Aspects, wherein the first feed stream comprises olefins and paraffins, and at least a portion of the olefins are removed from the first feed stream prior to feeding the first feed stream to the steam cracker furnace.

Aspect 31. The process for recycling plastic waste according to Aspect 30, wherein the olefins are removed from the first feed stream by contacting the first feed stream with sulfolane.

Aspect 32. The process for recycling plastic waste according to any of the preceding Aspects, wherein the pyrolysis oil is recycled to a refinery unit as a feedstock or co-feedstock.

Aspect 33. The process for recycling plastic waste according to any of the preceding Aspects, wherein the pyrolysis oil is recycled to refinery crude unit to produce circular naphtha or circular natural gas liquids (NGL).

Aspect 34. The process for recycling plastic waste according to any of the preceding Aspects, wherein the pyrolysis unit is co-located with the steam cracker furnace.

Aspect 35. The process for recycling plastic waste according to any of the preceding Aspects, wherein the pyrolysis unit is co-located with the separation unit.

Aspect 36. The process for recycling plastic waste according to any of the preceding Aspects, wherein the pyrolysis unit is located sufficiently close to the steam cracker furnace or the separation unit that the pyrolysis unit, the steam cracker furnace, and/or the separation unit are co-located on the same unit plot space within the same operating crew.

Aspect 37. The process for recycling plastic waste according to any of the preceding Aspects, wherein the pyrolysis unit is located sufficiently close to the steam cracker furnace or the separation unit that the $C_2$-$C_3$ fraction of the pyrolysis gas or the second condenser effluent can be supplied to the steam cracker furnace without additional compression or a pipeline.

Aspect 38. The process for recycling plastic waste according to any of the preceding Aspects, wherein the $C_2$-$C_3$ fraction of the pyrolysis gas or the second condenser effluent are not compressed and transported via pipeline to the steam cracker furnace.

Aspect 39. The process for recycling plastic waste according to any of Aspects 1-37, wherein the $C_2$-$C_3$ fraction of the pyrolysis gas or the second condenser effluent are compressed and transported via pipeline to the steam cracker furnace.

Aspect 40. The process for recycling plastic waste according to any of the preceding Aspects, further comprising the step of:

feeding at least a portion of the pyrolysis oil from the pyrolysis unit to the steam cracker furnace.

Aspect 41. The process for recycling plastic waste according to any of the preceding Aspects, wherein the first feed stream to the steam cracker furnace comprises Liquefied Petroleum Gas (LPG), Natural Gas Liquids (NGL), light ($C_2$-$C_5$) hydrocarbons, or naphtha ($C_6$-$C_{10}$).

Aspect 42. The process for recycling plastic waste according to any of the preceding Aspects, wherein the steam cracker feed comprises naphtha ($C_6$-$C_{10}$) and the pyrolysis oil.

Aspect 43. The process for recycling plastic waste according to any of the preceding Aspects, further comprising the step of:

feeding at least a portion of the ethylene effluent to one or more downstream processing units to provide a circular product selected from α-olefins such as normal-α-olefins ($C_4$-$C_{30}$+), ethylene homopolymers, ethylene-α-olefin copolymers, ethylene-normal-α-olefin ($C_4$-$C_{30}$+) copolymers, ethylene-propylene copolymers, ethylene-ionomer copolymers, chlorosulfonated polyethylene, vinyl chloride, ethylene oxide, ethylbenzene, acetaldehyde, vinyl acetate, or polyvinyl acetate.

Aspect 44. The process for recycling plastic waste according to Aspect 43, wherein:

the one or more downstream processing units provides circular vinyl chloride, and the circular vinyl chloride is fed to one or more subsequent processing units to provide a circular product selected from polyvinyl chloride homopolymers, polyvinyl chloride copolymers, vinyl chloride-vinyl acetate copolymers, 1,1,2-trichloroethane, vinylidene chloride, or polyvinylidene chloride.

Aspect 45. The process for recycling plastic waste according to Aspect 43, wherein:

the one or more downstream processing unit provides circular ethylene oxide, and the circular ethylene oxide is fed to one or more subsequent processing units to provide a circular product selected from ethylene glycol, poly(ethylene terephthalate), polyethylene glycol-polyalkylene glycol copolymers, ethoxylated phenols, ethoxylated amines, diethylene glycol, polyester, unsaturated polyester, polyester polyols, adipic acid, polyurethane resins, hydroxyethyl starch, hydroxyethyl gums, or hydroxyethyl cellulose.

Aspect 46. The process for recycling plastic waste according to Aspect 43, wherein:

the one or more downstream processing unit provides circular ethylbenzene, and the circular ethylbenzene is fed to one or more subsequent processing units to provide a circular product selected from styrene, polystyrene, styrene-butadiene copolymers, acrylonitrile-butadiene-styrene terpolymers, styrene-acrylonitrile copolymers, polyester resins, styrene-divinylbenzene resin, styrene-alkyd copolymers, or styrene-maleic anhydride copolymers.

Aspect 47. The process for recycling plastic waste according to Aspect 43, wherein:
the one or more downstream processing unit provides circular acetaldehyde, and
the circular acetaldehyde is fed to one or more subsequent processing units to provide a circular product selected from pentaerythritol, alkyd resins, or acetic acid.

Aspect 48. The process for recycling plastic waste according to Aspect 43, wherein:
the one or more downstream processing unit provides circular vinyl acetate, and
the circular vinyl acetate is fed to one or more subsequent processing units to provide a circular product selected from poly(vinyl acetate), poly(vinyl acetate) copolymers, ethylene-vinyl acetate copolymers, or vinyl chloride-vinyl acetate copolymers.

Aspect 49. The process for recycling plastic waste according to Aspect 43, wherein:
the one or more downstream processing unit provides circular poly(vinyl acetate) and
the circular poly(vinyl acetate) is fed to one or more subsequent processing units to provide a circular product selected from poly(vinyl alcohol), poly(vinyl butyral), poly(vinyl formal).

Aspect 50. The process for recycling plastic waste according to Aspect 43, wherein:
the one or more downstream processing unit provides circular α-olefin, and
the circular α-olefin is fed to one or more subsequent processing units to provide a circular product selected from poly-α-olefin or poly(ethylene-co-α-olefin).

Aspect 51. The process for recycling plastic waste according to Aspect 43, wherein:
the one or more downstream processing unit provides circular normal-α-olefins ($C_4$-$C_{30}$+), and
the circular normal-α-olefins ($C_4$-$C_{30}$+) is fed to one or more subsequent processing units to provide a circular product is selected from poly-(normal-α-olefin) or poly(ethylene-co-(normal-α-olefin)).

Aspect 52. The process for recycling plastic waste according to Aspect 43, wherein:
the circular α-olefin is selected from 1-butene, 1-pentene, 1-hexene, 1-heptene, 1-octene, 1-nonene, 1-decene, 1-dodecene, 1-tetradecene, 1-hexadecene, or 1-octadecene, and
the circular product is selected from poly(ethylene-co-1-butene), poly(ethylene-co-1-pentene), poly(ethylene-co-1-hexene), poly(ethylene-co-1-heptene), poly(ethylene-co-1-octene), poly(ethylene-co-1-nonene), poly(ethylene-co-1-decene), poly(ethylene-co-1-dodecene), poly(ethylene-co-1-tetradecene), poly(ethylene-co-1-hexadecene), or poly(ethylene-co-1-octadecene).

Aspect 53. The process for recycling plastic waste according to any of Aspects 1-52, further comprising the step of:
providing at least a portion of the ethylene effluent as a feed to a polymerization reactor to form a circular polyethylene.

Aspect 54. The process for recycling plastic waste according to any of Aspects 1-52, further comprising the step of:
providing at least a portion of the ethylene effluent as a feed for a catalyzed reaction with benzene to form circular ethylbenzene.

Aspect 55. The process for recycling plastic waste according to any of the preceding Aspects, further comprising the step of:
providing at least a portion of the ethylene effluent as a feed for a catalyzed reaction to form circular normal-α-olefins.

Aspect 56. The process for recycling plastic waste according to any of the preceding Aspects, further comprising the step of:
providing at least a portion of the ethylene effluent as a feed polymerization reactor for a catalyzed reaction with normal-α-olefins to form a circular ethylene-α-olefin copolymer.

Aspect 57. The process for recycling plastic waste according to any of Aspects 43-56, wherein the weight or fraction of the circular product which is attributable to the pyrolysis gas or plastic waste is determined by mass balance.

Aspect 58. The process for recycling plastic waste according to any of Aspects 43-57, further comprising the step of:
certifying any one or more of the circular products in accordance with International Sustainability and Carbon Certification (ISCC) standards, based upon the weight or fraction of the circular product attributable to the pyrolysis gas or the plastic waste, as determined by mass balance and the free attribution method.

Aspect 59. The process for recycling plastic waste according to any of the preceding Aspects, further comprising the step of:
feeding at least a portion of the propylene effluent to one or more downstream processing units to provide a circular product selected from polypropylene homopolymers, polypropylene copolymers, acrylonitrile, propylene oxide, cumene, n-butyraldehyde, isobutyraldehyde, allyl chloride, acrylic acid esters, or isopropyl alcohol.

Aspect 60. The process for recycling plastic waste according to Aspect 59, wherein:
the one or more downstream processing units provides circular acrylonitrile, and
the circular acrylonitrile is fed to one or more subsequent processing units to provide a circular product selected from polyacrylonitrile, modacrylic copolymers, acrylonitrile butadiene styrene (ABS), styrene acrylonitrile resin (SAN), nitrile elastomers, acrylonitrile copolymers, hexamethylene diamine, nylon 6,6, acrylamide, polyacrylamide homopolymers, or polyacrylamide copolymers.

Aspect 61. The process for recycling plastic waste according to Aspect 59, wherein:
the one or more downstream processing units provides circular propylene oxide, and
the circular propylene oxide is fed to one or more subsequent processing units to provide a circular product selected from propylene glycol, polyesters, poly(propylene glycols) homopolymers, poly(propylene glycols) copolymers, or polyurethanes.

Aspect 62. The process for recycling plastic waste according to Aspect 59, wherein:
the one or more downstream processing units provides circular n-butyraldehyde, and
the circular n-butyraldehyde is fed to one or more subsequent processing units to provide a circular product selected from poly(vinyl butyral), n-butyric acid, n-butyric anhydride, or cellulose acetate butyrate.

Aspect 63. The process for recycling plastic waste according to Aspect 59, wherein:
the one or more downstream processing units provides circular isobutyraldehyde, and the circular isobutyraldehyde is fed to one or more subsequent processing units to provide a circular product selected from neopentyl glycol, polyesters, or polyurethanes.

Aspect 64. The process for recycling plastic waste according to Aspect 59, wherein:

the one or more downstream processing units provides circular allyl chloride, and the circular allyl chloride is fed to one or more subsequent processing units to provide a circular product selected from epichlorohydrin or epoxy resins.

Aspect 65. The process for recycling plastic waste according to Aspect 59, wherein:

the one or more downstream processing units provides circular acrylic acid esters, and the circular acrylic acid esters are fed to one or more subsequent processing units to provide a circular product selected from acrylic homopolymers or copolymers.

Aspect 66. The process for recycling plastic waste according to Aspect 59, wherein:

the one or more downstream processing units provides circular isopropyl alcohol, and the circular isopropyl alcohol is fed to one or more subsequent processing units to provide a circular product selected from acetone, bisphenol A, epoxy resins, polycarbonates, polysulfones, methacrylic acid, poly(methyl methacrylate) homopolymers or poly(methyl methacrylate) copolymers.

Aspect 67. The process for recycling plastic waste according to any of the preceding Aspects, further comprising the step of:

providing at least a portion of the propylene effluent as a feed to a polymerization reactor to form a circular polypropylene.

Aspect 68. The process for recycling plastic waste according to any of Aspects 59-67, wherein the weight or fraction of the circular product which is attributable to the pyrolysis gas or plastic waste is determined by mass balance.

Aspect 69. The process for recycling plastic waste according to any of Aspects 59-68, further comprising the step of:

certifying any one or more of the circular products in accordance with International Sustainability and Carbon Certification (ISCC) standards, based upon the weight or fraction of the circular product attributable to the pyrolysis gas or the plastic waste, as determined by mass balance and the free attribution method.

Aspect 70. The process for recycling plastic waste according to any of the preceding Aspects, wherein the separating step provides circular products further comprising a butenes and butane effluent, the process further comprising the step of:

feeding at least a portion of the butenes and butane effluent to one or more downstream processing units to provide a circular product selected from circular butadiene, maleic anhydride, butylene oxide, 1-butene, mixed butenes, isobutene, or butane.

Aspect 71. The process for recycling plastic waste according to Aspect 70, wherein:

the one or more downstream processing units provides circular butadiene, and the circular butadiene is fed to one or more subsequent processing units to provide a circular product selected from circular styrene, polybutadiene elastomer, polybutadiene resins, hexamethylene diamine, nylons, chloroprene, neoprene elastomer, 1,5-cyclooctadiene, ethylene-propylene terpolymer elastomer, 1,5,9-cyclododecatriene, dodecanoic acid, nylon 6,12, qiana, lauryl lactam, nylon 12, OH-terminated polymers and copolymers, polyurethane elastomers, or 1,4-hexadiene.

Aspect 72. The process for recycling plastic waste according to Aspect 70, wherein:

the one or more downstream processing units provides circular maleic anhydride, and the circular maleic anhydride is fed to one or more subsequent processing units to provide a circular product selected from circular polyesters, alkyd resins, or styrene-maleic anhydride copolymer.

Aspect 73. The process for recycling plastic waste according to Aspect 70, wherein:

the one or more downstream processing units provides circular butylene oxide, and the circular butylene oxide is fed to one or more subsequent processing units to provide a circular product selected from circular poly(butylene oxide) or polyurethanes.

Aspect 74. The process for recycling plastic waste according to Aspect 70, wherein:

the one or more downstream processing units provides circular 1-butene, mixed butenes, and isobutene, and the circular 1-butene, mixed butenes, and isobutene is fed to one or more subsequent processing units to provide a circular product selected from circular poly(1-butene), poly(butene), poly(isobutene), or butyl rubber.

Aspect 75. The process for recycling plastic waste according to Aspect 70, wherein:

the one or more downstream processing units provides circular butane, and the circular butane is fed to one or more subsequent processing units to provide a circular product selected from circular acetic acid.

Aspect 76. The process for recycling plastic waste according to any of the preceding Aspects, wherein the pyrolysis unit is operated under conditions selected to increase, optimize, or maximize the proportion of pyrolysis gas in the pyrolysis unit effluent relative to pyrolysis liquid in the pyrolysis unit effluent.

Aspect 77. The process for recycling plastic waste according to any of the preceding Aspects, wherein the pyrolysis unit is operated under conditions selected to increase, optimize, or maximize the proportion of the $C_2$-$C_3$ fraction of the pyrolysis gas relative to the $C_4$-$C_5$ fraction of the pyrolysis gas.

Aspect 78. The process for recycling plastic waste according to any of the preceding Aspects, wherein the pyrolysis unit is operated under conditions selected to increase, optimize, or maximize proportion of ethylene in the pyrolysis gas.

Aspect 79. The process for recycling plastic waste according to any of the preceding Aspects, wherein the pyrolysis unit is operated under conditions selected to increase, optimize, or maximize the proportion of $C_5$ and lighter ($C_{\leq 5}$) hydrocarbons in the pyrolysis gas relative to $C_6$ and any heavier ($C_{\geq 6}$) hydrocarbons.

Aspect 80. The process for recycling plastic waste according to any of the preceding Aspects, wherein the plastic waste is processed in the pyrolysis unit at a temperature of from about 450° C. to about 800° C.

Aspect 81. The process for recycling plastic waste according to any of the preceding Aspects, wherein the plastic waste is processed in the pyrolysis unit at a temperature of from about 600° C. to about 800° C.

Aspect 82. The process for recycling plastic waste according to any of the preceding Aspects, wherein the plastic waste is processed in the pyrolysis unit under catalytic conditions in the presence of a catalyst.

Aspect 83. The process for recycling plastic waste according to any of the preceding Aspects, wherein the plastic waste is processed in the pyrolysis unit under catalytic conditions using a catalyst comprising alumina, aluminosilicates (for example, zeolites, or silica-alumina), silica-alumina-phosphates, transition metal oxides (for example, titania, zirconia, hafnia, or niobia), polyoxometallates, heteropolyoxometallates, polystyrene sulfonic acid resin, sulfonated carbon, solid phosphoric acid, or niobic acid.

Aspect 84. The process for recycling plastic waste according to any of the preceding Aspects, wherein the plastic waste is processed in the pyrolysis unit under non-catalytic conditions in the absence of a catalyst.

Aspect 85. The process for recycling plastic waste according to any of the preceding Aspects, wherein the pyrolysis unit operates continuously.

Aspect 86. The process for recycling plastic waste according to any of the preceding Aspects, wherein the pyrolysis unit operates intermittently.

Aspect 87. The process for recycling plastic waste according to any of the preceding Aspects, wherein the pyrolysis gas comprises from about 15 wt. % to about 40 wt. % of ethylene, or alternatively from about 18 wt. % to about 38 wt. % of ethylene.

Aspect 88. The process for recycling plastic waste according to any of the preceding Aspects, wherein the pyrolysis gas comprises from about 25 wt. % to about 60 wt. % of a $C_2$ hydrocarbon (ethane and ethylene), or alternatively from about 30 wt. % to about 55 wt. % of a $C_2$ hydrocarbon.

Aspect 89. The process for recycling plastic waste according to any of the preceding Aspects, wherein the pyrolysis gas comprises from about 15 wt. % to about 35 wt. % of propylene, or alternatively from about 17 wt. % to about 32 wt. % of propylene.

Aspect 90. The process for recycling plastic waste according to any of the preceding Aspects, wherein the pyrolysis gas comprises from about 17 wt. % to about 45 wt. % of a $C_3$ hydrocarbon (propane and propylene), or alternatively from about 20 wt. % to about 42 wt. % of a $C_3$ hydrocarbon.

Aspect 91. The process for recycling plastic waste according to any of the preceding Aspects, wherein the pyrolysis gas is purified prior to providing the separation unit feed comprising the pyrolysis gas to the separation unit.

Aspect 92. The process for recycling plastic waste according to any of the preceding Aspects, wherein the plastic waste comprises polyethylene, polypropylene, polystyrene, polyethylene terephthalate (PET), polyvinyl chloride (PVC), polyamide, polycarbonate, polyurethane, polyester, copolymers thereof, filled polymers thereof, composites thereof, natural or synthetic rubber, tires, or any combination thereof.

Aspect 93. The process for recycling plastic waste according to any of the preceding Aspects, wherein the plastic waste comprises a chloride-containing polymer, at least a portion of which has been removed from the plastic waste prior to pyrolyzing the plastic waste in the pyrolysis unit.

Aspect 94. The process for recycling plastic waste according to any of the preceding Aspects, wherein the plastic waste comprises polyethylene, polypropylene, polystyrene, polyethylene terephthalate (PET), polyamide, polycarbonate, polyurethane, or polyester.

Aspect 95. The process for recycling plastic waste according to any of the preceding Aspects, wherein the pyrolysis gas or the pyrolysis oil comprises non-hydrocarbon contaminants.

Aspect 96. The process for recycling plastic waste according to any of the preceding Aspects, wherein the pyrolysis gas or the pyrolysis oil comprises a non-hydrocarbon contaminant selected from an inorganic acid, an organic acid, a binary compound of a group 15 element and hydrogen, a binary compound of a group 16 element and hydrogen, an organic compound comprising a group 15 element, or an organic compound comprising a group 16 element.

Aspect 97. The process for recycling plastic waste according to any of the preceding Aspects, wherein the pyrolysis gas or the pyrolysis oil comprises a non-hydrocarbon contaminant selected from an HCl, HBr, phosphine, arsine, stibine, an alcohol, an organic acid, a nitrogen oxide, chloroform, a $C_1$-$C_3$ hydrocarbon chloride, or a $C_1$-$C_3$ hydrocarbon fluoride.

Aspect 98. The process for recycling plastic waste according to any of the preceding Aspects, wherein the pyrolysis gas is pretreated with caustic or an amine (a) prior to feeding the pyrolysis gas to the separation unit, or (b) prior to feeding the pyrolysis gas to the condensing unit.

Aspect 99. The process for recycling plastic waste according to any of the preceding Aspects, wherein the pyrolysis gas is pretreated with metal oxide catalyst bed (a) prior to feeding the pyrolysis gas to the separation unit, or (b) prior to feeding the pyrolysis gas to the condensing unit.

Aspect 100. The process for recycling plastic waste according to Aspect 99, wherein the metal oxide catalyst bed is selected from zinc oxide, calcium oxide, or iron oxide.

Aspect 101. The process for recycling plastic waste according to any of the preceding Aspects, wherein the pyrolysis gas is pretreated with a molecular sieve or a promoted or activated alumina (a) prior to feeding the pyrolysis gas to the separation unit, or (b) prior to feeding the pyrolysis gas to the condensing unit.

Aspect 102. The process for recycling plastic waste according to any of the preceding Aspects, further comprising the step of feeding at least a portion of the ethylene effluent to a polymerization reactor to form a circular polyethylene, wherein the amount of circular polyethylene produced is at least 10% greater than the amount of circular polyethylene produced in a corresponding process that uses a liquid pyrolysis effluent feedstock only, as quantified by a percent (%) of gas yield from the pyrolysis unit per unit weight of plastic feed.

Aspect 103. The process for recycling plastic waste according to Aspect 102, wherein the amount of circular polyethylene produced is at least 15% greater than the amount of circular polyethylene produced in a corresponding process that uses a liquid pyrolysis effluent feedstock only, as quantified by a percent (%) of gas yield from the pyrolysis unit per unit weight of plastic feed.

Aspect 104. The process for recycling plastic waste according to Aspect 103, wherein the amount of circular polyethylene produced is from about 10% greater to about 25% greater than the amount of circular polyethylene produced in a corresponding process that uses a liquid pyrolysis effluent feedstock only, as quantified by a percent (%) of gas yield from the pyrolysis unit per unit weight of plastic feed.

Aspect 105. The process for recycling plastic waste according to any of Aspects 1-104, wherein a carbon footprint of any independently selected circular product is reduced by about 15% to about 40% as compared to a carbon footprint a corresponding non-circular product produced in the absence of the pyrolysis gas and the pyrolysis oil.

Aspect 106. The process for recycling plastic waste according to any of Aspects 1-104, wherein a carbon footprint of any independently selected circular product is reduced by about 20% to about 35% as compared to a carbon footprint a corresponding non-circular product produced in the absence of the pyrolysis gas and the pyrolysis oil.

Aspect 107. The process for recycling plastic waste according to any of Aspects 1-104, wherein a carbon footprint of any independently selected circular product is reduced by about 25% to about 30% as compared to a carbon footprint a corresponding non-circular product produced in the absence of the pyrolysis gas and the pyrolysis oil.

Aspect 108. The process for recycling plastic waste according to any of Aspects 1-107, wherein the plastic waste is pyrolyzed in an amount sufficient to displace up to about 5 wt % of a virgin feedstock required to produce the same amount of the ethylene effluent, the propylene effluent, and the light ($C_2$-$C_3$) saturated hydrocarbon effluent.

Aspect 109. The process for recycling plastic waste according to any of Aspects 1-107, wherein the plastic waste is pyrolyzed in an amount sufficient to displace from about 1 wt % to about 10 wt % of a virgin feedstock required to produce the same amount of the ethylene effluent, the propylene effluent, and the light ($C_2$-$C_3$) saturated hydrocarbon effluent.

Aspect 110. The process for recycling plastic waste according to any of Aspects 1-107, wherein the plastic waste is pyrolyzed in an amount sufficient to provide up to about 5 wt % of the separation unit feed.

Aspect 111. The process for recycling plastic waste according to any of Aspects 1-107, wherein the plastic waste is pyrolyzed in an amount sufficient to provide from about 1 wt % to about 10 wt % of the separation unit feed.

Aspect 112. A process for recycling plastic waste, the process comprising:
(a) pyrolyzing a plastic waste in a pyrolysis unit to produce a pyrolysis unit effluent comprising a pyrolysis gas and a pyrolysis oil and separating the pyrolysis gas from the pyrolysis oil, wherein the pyrolysis gas comprises $C_5$ and lighter ($C_{\leq 5}$) hydrocarbons having a $C_2$-$C_3$ fraction and a $C_4$-$C_5$ fraction;
(b) feeding a heavy hydrocarbon feed stream to a fluid catalytic cracker (FCC) reactor to produce an FCC effluent comprising naphtha ($C_6$-$C_{10}$ hydrocarbons) and $C_5$ and lighter ($C_{\leq 5}$) hydrocarbons;
(c) providing a fractionation unit feed comprising at least a portion of the pyrolysis gas and at least a portion of the FCC effluent to a fractionation unit; and
(d) separating the fractionation unit feed to provide circular products comprising a first fractionation effluent comprising $C_5$ and lighter ($C_{\leq 5}$) hydrocarbons and a second fractionation effluent comprising heavy ($C_{6+}$) hydrocarbons.

Aspect 113. The process for recycling plastic waste according to Aspect 112, wherein the pyrolysis gas is fed directly to the fractionation unit.

Aspect 114. The process for recycling plastic waste according to Aspect 112, wherein the FCC effluent and the pyrolysis gas are combined to form the fractionation unit feed prior being fed to the fractionation unit.

Aspect 115. The process for recycling plastic waste according to any of Aspects 112-114, wherein the heavy hydrocarbon feed stream is fed to a fluid catalytic cracker (FCC) pretreater to form a treated stream, prior to feeding the treated stream to the FCC reactor.

Aspect 116. The process for recycling plastic waste according to Aspect 115, wherein the treated stream has a lower sulfur content, a lower aromatic content, or both, as compared with the sulfur content and/or aromatic content in the heavy hydrocarbon feed stream.

Aspect 117. The process for recycling plastic waste according to any of Aspects 112-116, wherein the fractionation unit feed further comprises at least a portion of the pyrolysis oil.

Aspect 118. The process for recycling plastic waste according to any of Aspects 112-117, further comprising the step of:
recycling at least a portion of the second fractionation effluent comprising heavy ($C_{6+}$) hydrocarbons to the fluid catalytic cracker (FCC) reactor.

Aspect 119. The process for recycling plastic waste according to any of Aspects 112-117, further comprising the step of:
feeding at least a portion of the second fractionation effluent comprising heavy ($C_{6+}$) hydrocarbons to a reforming unit or an AROMAX® unit to provide a reforming product stream or an AROMAX® product stream, respectively, each comprising circular aromatic hydrocarbons.

Aspect 120. The process for recycling plastic waste according to Aspect 119, wherein:
the reforming product stream or the AROMAX® product stream comprises circular benzene, and
the circular benzene is fed to one or more subsequent processing units to provide a circular product selected from ethylbenzene, benzenesulfonic acid, chlorobenzene, cumene, cyclohexane, nitrobenzene, or maleic anhydride.

Aspect 121. The process for recycling plastic waste according to Aspect 119, wherein:
the reforming product stream or the AROMAX® product stream comprises circular toluene, and
the circular toluene is fed to one or more subsequent processing units to provide a circular product selected from dinitrotoluenes, toluene diisocyanate, or urethanes.

Aspect 122. The process for recycling plastic waste according to Aspect 119, wherein:
the reforming product stream or the AROMAX® product stream comprises circular o-xylene, and
the circular o-xylene is fed to one or more subsequent processing units to provide a circular product selected from phthalic anhydride, alkyd resins, polyester resins, polyester polyols, urethanes, or polyurethanes.

Aspect 123. The process for recycling plastic waste according to Aspect 119, wherein:
the reforming product stream or the AROMAX® product stream comprises circular m-xylene, and
the circular m-xylene is fed to one or more subsequent processing units to provide a circular product selected from isophthalic acid, polyesters, alkyd resins, polyamide resins, diphenyl isophthalate, or polybenzimidazoles.

Aspect 124. The process for recycling plastic waste according to Aspect 119, wherein:
the reforming product stream or the AROMAX® product stream comprises circular p-xylene, and
the circular p-xylene is fed to one or more subsequent processing units to provide a circular product selected from terephthalic acid, poly(ethylene terephthalate), or poly(butylene terephthalate).

Aspect 125. The process for recycling plastic waste according to any of Aspects 119-124, wherein the reforming product stream or the AROMAX® product stream further comprise hydrogen and aliphatic hydrocarbons.

Aspect 126. The process for recycling plastic waste according to any of Aspects 119-125, wherein the fraction of aromatic hydrocarbons in the reforming product stream or the AROMAX® product stream attributable to the plastic waste or pyrolysis gas is determined by mass balance.

Aspect 127. The process for recycling plastic waste according to any of Aspects 119-126, wherein the fraction of benzene, toluene, o-xylene, m-xylene, p-xylene, or any circular product produced in the one or more subsequent processing units attributable to the plastic waste or pyrolysis gas is determined by mass balance.

Aspect 128. The process for recycling plastic waste according to any of Aspects 119-127, further comprising the step of certifying the benzene, toluene, o-xylene, m-xylene, p-xylene, or any circular product produced in the one or more subsequent processing units attributable to the plastic waste or pyrolysis gas as circular in accordance with International Sustainability and Carbon Certification (ISCC) standards, based upon the weight or fraction of the circular product attributable to the plastic waste, as determined by mass balance and the free attribution method.

Aspect 129. The process for recycling plastic waste according to any of Aspects any one of Aspects 112-128, further comprising the step of feeding at least a portion of the first fractionation effluent comprising $C_5$ and lighter ($C_{\leq 5}$) hydrocarbons to a steam cracking furnace to form a steam cracker product stream comprising ethylene and light ($C_2$-$C_3$) saturated hydrocarbons.

Aspect 130. The process for recycling plastic waste according to Aspect 129, further comprising the steps of:
feeding the steam cracker product stream as a feed to a separation unit; and
separating the separation unit feed to provide an ethylene effluent, a propylene effluent, and a light ($C_2$-$C_3$) saturated hydrocarbon effluent.

Aspect 131. The process for recycling plastic waste according to Aspect 130, further comprising the step of:
feeding at least a portion of the ethylene effluent or the propylene effluent to a polymerization reactor to form a circular polyethylene or a circular polypropylene.

Aspect 132. The process for recycling plastic waste according to any of Aspects 130-131, wherein the fraction of ethylene in the ethylene effluent, propylene in the propylene effluent, polyethylene, or polypropylene attributable to the plastic waste or the pyrolysis gas is determined by mass balance.

Aspect 131. The process for recycling plastic waste according to any of Aspects 130-132, further comprising the step of
recycling at least a portion of the light ($C_2$-$C_3$) saturated hydrocarbon effluent to the steam cracking furnace.

We claim:

1. A process for recycling plastic waste, the process comprising:
    (a) pyrolyzing a plastic waste in a pyrolysis unit under a first set of pyrolysis conditions to produce a pyrolysis unit effluent comprising a pyrolysis gas and a pyrolysis oil in a known ratio and separating the pyrolysis gas from the pyrolysis oil, wherein the pyrolysis gas comprises $C_5$ and lighter ($C_1$, $C_2$, $C_3$, $C_4$, and $C_5$) hydrocarbons, including ethylene, propylene, and butylene (EPB);
    (b) feeding a first feed stream to a steam cracker furnace to produce a steam cracker furnace effluent comprising ethylene, propylene, and light ($C_2$-$C_3$) saturated hydrocarbons;
    (c) providing to a separation unit a separation unit feed comprising at least a portion of the pyrolysis gas and at least a portion of the steam cracker furnace effluent; and
    (d) separating the separation unit feed to provide circular products comprising an ethylene effluent, a propylene effluent, and a light ($C_2$-$C_3$) saturated hydrocarbon effluent.

2. A process for recycling plastic waste according to claim 1, the process further comprising the steps of:
    (a') assigning a market price to the pyrolysis oil formed under the first set of pyrolysis conditions as equivalent to a market price of a reference liquid product;
    (b') determining a market price of the combined ethylene, propylene, and butylene (EPB) in the pyrolysis gas formed under the first set of pyrolysis conditions; and
    (c') (1) when the market price of the combined EPB is greater than the market price of the pyrolysis oil, applying a second set of pyrolysis conditions which increase the proportion of pyrolysis gas relative to the pyrolysis oil in the pyrolysis reactor effluent; or (2) when the market price of the pyrolysis oil is greater than the market price of the combined EPB formed under the first set of conditions, applying a second set of pyrolysis conditions which increase the proportion of pyrolysis oil relative to the pyrolysis gas in the pyrolysis reactor effluent.

3. The process for recycling plastic waste according to claim 2, wherein the pyrolysis oil comprises distillation cuts, and assigning a market price to the pyrolysis oil comprises assigning a market price to each distillation cut in the pyrolysis oil as equal to a market price of an equivalent reference liquid product for each distillation cut.

4. The process for recycling plastic waste according to claim 3, wherein the market price of the pyrolysis oil comprises a weighted average of the equivalent reference liquid product for each distillation cut.

5. The process for recycling plastic waste according to claim 3, wherein the distillation cuts of the pyrolysis oil comprise any combination of distillation cuts selected from diesel, gasoline, naphtha, kerosene, gas oil, and waxes.

6. The process for recycling plastic waste according to claim 2, wherein the reference liquid product comprises gasoline, diesel, or a blend of gasoline and diesel.

7. The process for recycling plastic waste according to claim 2, wherein the reference liquid product comprises a blend of gasoline and diesel having about 95 wt % to 5 wt % gasoline and about 5 wt % to 95 wt % diesel.

8. The process for recycling plastic waste according to claim 1, further comprising the step of:
recycling at least a portion of the light ($C_2$-$C_3$) saturated hydrocarbon effluent to the steam cracking furnace.

9. The process for recycling plastic waste according to claim 1, wherein the pyrolysis oil is recycled to a refinery unit as a feedstock or co-feedstock or recycled to refinery crude unit to produce circular naphtha or circular natural gas liquids (NGL).

10. The process for recycling plastic waste according to claim 1, wherein the pyrolysis unit is co-located with the steam cracker furnace.

11. The process for recycling plastic waste according to claim 1, further comprising the step of:
feeding at least a portion of the pyrolysis oil from the pyrolysis unit to the steam cracker furnace.

12. The process for recycling plastic waste according to claim 1, wherein the first feed stream to the steam cracker furnace comprises Liquefied Petroleum Gas (LPG), Natural Gas Liquids (NGL), light ($C_2$-$C_5$) hydrocarbons, naphtha ($C_6$-$C_{10}$), or the pyrolysis oil.

13. The process for recycling plastic waste according to claim 1, further comprising the step of:

feeding at least a portion of the ethylene effluent to one or more downstream processing units to provide a circular product comprising one or more normal-α-olefins ($C_4$-$C_{30}+$), one or more ethylene homopolymers, one or more ethylene-α-olefin copolymers, one or more ethylene-normal-α-olefin ($C_4$-$C_{30}+$) copolymers, one or more ethylene-propylene copolymers, one or more ethylene-ionomer copolymers, chlorosulfonated polyethylene, vinyl chloride, ethylene oxide, ethylbenzene, acetaldehyde, vinyl acetate, or polyvinyl acetate.

14. The process for recycling plastic waste according to claim 1, wherein:
the one or more downstream processing unit provides a circular α-olefin selected from 1-butene, 1-pentene, 1-hexene, 1-heptene, 1-octene, 1-nonene, 1-decene, 1-dodecene, 1-tetradecene, 1-hexadecene, or 1-octadecene; and
the circular α-olefin is fed to one or more subsequent processing units to provide a circular product selected from a poly-α-olefin or a poly(ethylene-co-α-olefin).

15. The process for recycling plastic waste according to claim 1, further comprising the step of:
providing at least a portion of the ethylene effluent as a feed for a catalyzed reaction to form a circular polyethylene, circular ethylbenzene, circular normal-α-olefins, or circular ethylene-α-olefin copolymer.

16. The process for recycling plastic waste according to claim 1, further comprising the step of:
feeding at least a portion of the propylene effluent to one or more downstream processing units to provide a circular product selected from polypropylene homopolymers, polypropylene copolymers, acrylonitrile, propylene oxide, cumene, n-butyraldehyde, isobutyraldehyde, allyl chloride, acrylic acid esters, or isopropyl alcohol.

17. The process for recycling plastic waste according to claim 1, wherein the separating step provides circular products further comprising a butenes and butane effluent, the process further comprising the step of:
feeding at least a portion of the butenes and butane effluent to one or more downstream processing units to provide a circular product selected from circular butadiene, maleic anhydride, butylene oxide, 1-butene, mixed butenes, isobutene, or butane.

18. The process for recycling plastic waste according to claim 1, wherein the pyrolysis unit is operated under conditions selected to increase, optimize, or maximize the proportion of pyrolysis gas in the pyrolysis unit effluent relative to pyrolysis liquid in the pyrolysis unit effluent.

19. The process for recycling plastic waste according to claim 1, wherein the plastic waste is processed in the pyrolysis unit at a temperature of from about 450° C. to about 800° C.

20. The process for recycling plastic waste according to claim 1, wherein the plastic waste is processed in the pyrolysis unit under catalytic conditions in the presence of a catalyst comprising alumina, aluminosilicates, silica-alumina-phosphates, transition metal oxides, polyoxometallates, heteropolyoxometallates, polystyrene sulfonic acid resin, sulfonated carbon, solid phosphoric acid, or niobic acid.

21. The process for recycling plastic waste according to claim 1, wherein the plastic waste comprises polyethylene, polypropylene, polystyrene, polyethylene terephthalate (PET), polyvinyl chloride (PVC), polyamide, polycarbonate, polyurethane, polyester, copolymers thereof, filled polymers thereof, composites thereof, natural or synthetic rubber, tires, or any combination thereof.

22. The process for recycling plastic waste according to claim 1, further comprising the step of feeding at least a portion of the ethylene effluent to a polymerization reactor to form a circular polyethylene,
wherein the amount of circular polyethylene produced is at least 10% greater than the amount of circular polyethylene produced in a corresponding process that uses a liquid pyrolysis effluent feedstock only, as quantified by a percent (%) of gas yield from the pyrolysis unit per unit weight of plastic feed.

23. The process for recycling plastic waste according to claim 1, wherein the weight or fraction of the circular products which is attributable to the pyrolysis gas or plastic waste is determined by mass balance.

24. The process for recycling plastic waste according to claim 1, further comprising the step of:
certifying any one or more of the circular products from the separation unit as a circular product in accordance with International Sustainability and Carbon Certification (ISCC) standards, based upon the weight or fraction of the circular product attributable to the pyrolysis gas or the plastic waste, as determined by mass balance and the free attribution method.

25. A process for recycling plastic waste, the process comprising:
(a) pyrolyzing a plastic waste in a pyrolysis unit under a first set of pyrolysis conditions to produce a pyrolysis unit effluent comprising a pyrolysis gas and a pyrolysis oil in a known ratio and separating the pyrolysis gas from the pyrolysis oil, wherein the pyrolysis gas comprises $C_5$ and lighter ($C_1$, $C_2$, $C_3$, $C_4$, and $C_5$) hydrocarbons, including ethylene, propylene, and butylene (EPB);
(b) providing the pyrolysis gas to a condensing unit and forming a first condenser effluent having a higher proportion of $C_4$-$C_5$ hydrocarbons than the pyrolysis gas and a second condenser effluent having a higher proportion of $C_2$-$C_3$ hydrocarbons than the pyrolysis gas;
(c) feeding a first feed stream to a steam cracker furnace to produce a steam cracker furnace effluent comprising ethylene, propylene, and light ($C_2$-$C_3$) saturated hydrocarbons;
(d) providing to a separation unit a separation unit feed comprising at least a portion of the second condenser effluent and at least a portion of the steam cracker furnace effluent; and
(e) separating the separation unit feed to provide circular products comprising an ethylene effluent, a propylene effluent, and a light ($C_2$-$C_3$) saturated hydrocarbon effluent.

26. A process for recycling plastic waste according to claim 25, the process further comprising the steps of:
(a') assigning a market price to the pyrolysis oil formed under the first set of pyrolysis conditions as equivalent to a market price of a reference liquid product;
(b') determining a market price of the combined ethylene, propylene, and butylene (EPB) in the pyrolysis gas formed under the first set of pyrolysis conditions; and
(c') (1) when the market price of the combined EPB is greater than the market price of the pyrolysis oil, applying a second set of pyrolysis conditions which increase the proportion of pyrolysis gas relative to the pyrolysis oil in the pyrolysis reactor effluent; or (2) when the market price of the pyrolysis oil is greater than the market price of the combined EPB formed under the first set of conditions, applying a second set of pyrolysis conditions which increase the proportion of pyrolysis oil relative to the pyrolysis gas in the pyrolysis reactor effluent.

27. The process for recycling plastic waste according to claim 26, wherein the pyrolysis oil comprises distillation cuts, and assigning a market price to the pyrolysis oil comprises assigning a market price to each distillation cut in the pyrolysis oil as equal to a market price of an equivalent reference liquid product for each distillation cut.

28. The process for recycling plastic waste according to claim 27, wherein:
the market price of the pyrolysis oil comprises a weighted average of the equivalent reference liquid product for each distillation cut; and
the distillation cuts of the pyrolysis oil comprise any combination of distillation cuts selected from diesel, gasoline, naphtha, kerosene, gas oil, and waxes.

29. The process for recycling plastic waste according to claim 25, further comprising the step of:
feeding at least a portion of the ethylene effluent to one or more downstream processing units to provide a circular product comprising one or more normal-α-olefins ($C_4$-$C_{30}$+), one or more ethylene homopolymers, one or more ethylene-α-olefin copolymers, one or more ethylene-normal-α-olefin ($C_4$-$C_{30}$+) copolymers, one or more ethylene-propylene copolymers, one or more ethylene-ionomer copolymers, chlorosulfonated polyethylene, vinyl chloride, ethylene oxide, ethylbenzene, acetaldehyde, vinyl acetate, or polyvinyl acetate.

30. The process for recycling plastic waste according to claim 25, further comprising the step of:
certifying any one or more of the circular products from the separation unit as a circular product in accordance with International Sustainability and Carbon Certification (ISCC) standards, based upon the weight or fraction of the circular product attributable to the pyrolysis gas or the plastic waste, as determined by mass balance and the free attribution method.

31. A process for recycling plastic waste, the process comprising:
(a) pyrolyzing a plastic waste in a pyrolysis unit to produce a pyrolysis unit effluent comprising a pyrolysis gas and a pyrolysis oil and separating the pyrolysis gas from the pyrolysis oil, wherein the pyrolysis gas comprises $C_5$ and lighter ($C_{\leq 5}$) hydrocarbons having a $C_2$-$C_3$ fraction and a $C_4$-$C_5$ fraction;
(b) feeding a heavy hydrocarbon feed stream to a fluid catalytic cracker (FCC) reactor to produce an FCC effluent comprising naphtha ($C_6$-$C_{10}$ hydrocarbons) and $C_5$ and lighter ($C_{\leq 5}$) hydrocarbons;
(c) providing a fractionation unit feed comprising at least a portion of the pyrolysis gas and at least a portion of the FCC effluent to a fractionation unit; and
(d) separating the fractionation unit feed to provide circular products comprising a first fractionation effluent comprising $C_5$ and lighter ($C_{\leq 5}$) hydrocarbons and a second fractionation effluent comprising heavy ($C_{6+}$) hydrocarbons.

32. The process for recycling plastic waste according to claim 31, wherein the fractionation unit feed further comprises at least a portion of the pyrolysis oil.

33. The process for recycling plastic waste according to claim 31, further comprising the step of:
recycling at least a portion of the second fractionation effluent comprising heavy ($C_{6+}$) hydrocarbons to the fluid catalytic cracker (FCC) reactor.

34. The process for recycling plastic waste according to claim 31, further comprising the step of:
feeding at least a portion of the second fractionation effluent comprising heavy ($C_{6+}$) hydrocarbons to a reforming unit or an AROMAX® unit to provide a reforming product stream or an AROMAX® product stream, respectively, each comprising circular aromatic hydrocarbons.

35. The process for recycling plastic waste according to claim 31, wherein:
the reforming product stream or the AROMAX® product stream comprises circular products selected from benzene, toluene, o-xylene, m-xylene, or p-xylene; and
at least one circular product is fed to one or more subsequent processing units to provide a subsequent circular product selected from ethylbenzene, benzenesulfonic acid, chlorobenzene, cumene, cyclohexane, nitrobenzene, maleic anhydride, dinitrotoluenes, toluene diisocyanate, urethanes, phthalic anhydride, alkyd resins, polyester resins, polyester polyols, urethanes, polyurethanes, isophthalic acid, polyamide resins, diphenyl isophthalate, polybenzimidazoles, terephthalic acid, poly(ethylene terephthalate), or poly(butylene terephthalate).

36. The process for recycling plastic waste according to claim 31, further comprising the steps of:
feeding at least a portion of the first fractionation effluent comprising $C_5$ and lighter ($C_{\leq 5}$) hydrocarbons to a steam cracking furnace to form a steam cracker product stream comprising ethylene and light ($C_2$-$C_3$) saturated hydrocarbons;
feeding the steam cracker product stream as a feed to a separation unit;
separating the separation unit feed to provide an ethylene effluent, a propylene effluent, and a light ($C_2$-$C_3$) saturated hydrocarbon effluent; and
feeding at least a portion of the ethylene effluent or the propylene effluent to a polymerization reactor to form a circular polyethylene or a circular polypropylene.

* * * * *